United States Patent
Inoue et al.

(10) Patent No.: US 9,695,158 B2
(45) Date of Patent: Jul. 4, 2017

(54) DIBENZO[F,H]QUINOXALINE DERIVATIVE, METHOD OF SYNTHESIZING THE SAME, LIGHT-EMITTING ELEMENT, LIGHT-EMITTING DEVICE, ELECTRONIC APPLIANCE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomohiro Kubota, Kanagawa (JP); Satoshi Seo, Kanagawa (JP); Hayato Yamawaki, Kanagawa (JP); Yasushi Kitano, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 14/484,693

(22) Filed: Sep. 12, 2014

(65) Prior Publication Data
US 2015/0080574 A1 Mar. 19, 2015

(30) Foreign Application Priority Data

Sep. 13, 2013 (JP) .................................. 2013-190214
May 9, 2014 (JP) .................................. 2014-097738

(51) Int. Cl.
C07D 409/10 (2006.01)
H01L 51/50 (2006.01)
H01L 51/00 (2006.01)

(52) U.S. Cl.
CPC ........ *C07D 409/10* (2013.01); *H01L 51/0072* (2013.01); *H01L 51/0074* (2013.01); *H01L 51/5012* (2013.01)

(58) Field of Classification Search
CPC ............ H01L 51/0072; H01L 51/0074; H01L 51/5012; C07D 409/10; G06Q 30/02; G06Q 30/0269; G06Q 50/01
USPC ............................................ 544/343; 257/40
See application file for complete search history.

(56) References Cited

U.S. PATENT DOCUMENTS

| | | | |
|---|---|---|---|
| 7,355,340 B2 * | 4/2008 | Shitagaki et al. | 313/504 |
| 8,981,366 B2 * | 3/2015 | Kadoma et al. | 257/40 |
| 9,079,879 B2 * | 7/2015 | Kadoma | C07D 403/10 |
| 2011/0210316 A1 * | 9/2011 | Kadoma | C07D 403/10 |
| | | | 257/40 |
| 2013/0323869 A1 | 12/2013 | Inoue et al. | |
| 2013/0324729 A1 | 12/2013 | Inoue et al. | |

FOREIGN PATENT DOCUMENTS

EP  2 363 398 A1  9/2011
JP  2011-201869  10/2011

* cited by examiner

*Primary Examiner* — Valerie Rodriguez-Garcia
(74) *Attorney, Agent, or Firm* — Husch Blackwell LLP

(57) ABSTRACT

A composition comprising a dibenzo[f,h]quinoxaline derivative in which impurities are reduced and a method of synthesizing dibenzo[f,h]quinoxaline in which impurities are reduced are provided. In addition, a light-emitting element, a light-emitting device, an electronic appliance, or a lighting device with high emission efficiency and high reliability in which dibenzo[f,h]quinoxaline is used as an EL material is provided. In the synthesis method, 2-(chloroaryl) dibenzo[f,h]quinoxaline is used as a synthetic intermediate in a synthetic pathway so that an impurity contained in a final product can be removed easily by purification by sublimation.

1 Claim, 12 Drawing Sheets

DIBENZO[F,H]QUINOXALINE DERIVATIVE, METHOD OF SYNTHESIZING THE SAME, LIGHT-EMITTING ELEMENT, LIGHT-EMITTING DEVICE, ELECTRONIC APPLIANCE, AND LIGHTING DEVICE

BACKGROUND OF THE INVENTION

1. Field of the Invention

The present invention relates to an object, a method, or a fabrication method. In addition, the present invention relates to a process, a machine, manufacture, or a composition of matter. In particular, one embodiment of the present invention relates to a semiconductor device, a display device, a light-emitting device, a driving method thereof, or a fabrication method thereof. In particular, one embodiment of the present invention relates to a dibenzo[f,h]quinoxaline derivative and a novel method of synthesizing the same. In addition, one embodiment of the present invention relates to a light-emitting element, a light-emitting device, an electronic appliance, and a lighting device that include the dibenzo[f,h]quinoxaline derivative.

2. Description of the Related Art

A light-emitting element with a structure in which an EL layer is provided between a pair of electrodes is a self-luminous light-emitting element in which carriers (holes and electrons) are injected from the pair of electrodes by application of an electric field and recombined in the EL layer to generate energy, so that light is emitted.

An organic compound is mainly used as an EL material for an EL layer in a light-emitting element and greatly contributes to an improvement in the characteristics of the light-emitting element. For this reason, a variety of novel organic compounds have been developed (e.g., Patent Document 1).

REFERENCE

Patent Document 1: Japanese Published Patent Application No. 2011-201869

SUMMARY OF THE INVENTION

In a synthesis of an organic compound, a simple and inexpensive method is preferably employed, but the important thing is that contained substances (impurities) that cannot be removed technically be as few as possible. As a method of synthesizing, for example, a dibenzo[f,h]quinoxaline derivative, a synthesis method in which a monochlorinated dibenzo[f,h]quinoxaline derivative is used as a source material is known (e.g., Patent Document 1). However, in this synthesis method, a dibenzo[f,h]quinoxaline derivative having a plurality of chlorine atoms is likely to be contained as an impurity. Such an impurity is difficult to remove and might be mixed in a final product.

Note that in fabrication of a light-emitting element, formation of an EL layer affects characteristics of the light-emitting element and is thus very important. When an impurity such as a chloride is contained in an EL material used for the EL layer, the characteristics of the light-emitting element are degraded.

In view of the above, one embodiment of the present invention provides a dibenzo[f,h]quinoxaline derivative in which impurities are reduced and a novel method of synthesizing the dibenzo[f,h]quinoxaline derivative in which impurities are reduced. Another embodiment of the present invention provides a light-emitting element, a light-emitting device, an electronic appliance, or a lighting device with high emission efficiency and high reliability in which the dibenzo[f,h]quinoxaline derivative is used as an EL material. Another embodiment of the present invention provides a novel material. Another embodiment of the present invention provides a novel light-emitting element and a novel light-emitting device. Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a method of synthesizing a dibenzo[f,h]quinoxaline derivative that can reduce impurities and a dibenzo[f,h]quinoxaline derivative in which impurities are reduced. In the synthesis method, a 2-(chloroaryl)dibenzo[f,h]quinoxaline derivative is used as a synthetic intermediate in a synthetic pathway so that an impurity contained in a final product can be removed easily by purification by sublimation.

Note that in the synthesis method, a 2-chlorodibenzo[f,h]quinoxaline derivative and a chloroaryl boronic acid are coupled to obtain the 2-(chloroaryl)dibenzo[f,h]quinoxaline derivative as a synthetic intermediate. At this time, an impurity in which a dibenzo[f,h]quinoxaline skeleton of the 2-chlorodibenzo[f,h]quinoxaline derivative is substituted by a plurality of chlorine atoms is contained. However, by a chemical reaction, the plurality of chlorine atoms of the dibenzo[f,h]quinoxaline skeleton are substituted by a chloroaryl group or a hydrogen atom. Then, the 2-(chloroaryl)dibenzo[f,h]quinoxaline derivative obtained through this reaction and an aryl boronic acid or a heteroaryl boronic acid are coupled. In this manner, a dibenzo[f,h]quinoxaline derivative in which impurities are reduced can be produced as a final product. One embodiment of the present invention includes such a synthesis method. In addition, one embodiment of the present invention includes the 2-(chloroaryl)dibenzo[f,h]quinoxaline derivative serving as a synthetic intermediate.

Thus, one embodiment of the present invention is a dibenzo[f,h]quinoxaline derivative in which the 2-position of a dibenzo[f,h]quinoxaline skeleton is bonded to an aryl group. The aryl group has at least one aryl group or heteroaryl group as a substituent. The chlorine content of the dibenzo[f,h]quinoxaline derivative is 10 ppm or less.

Another embodiment of the present invention is a dibenzo[f,h]quinoxaline derivative represented by General Formula (G1) that has a chlorine content of 10 ppm or less.

[Chemical Formula 1]

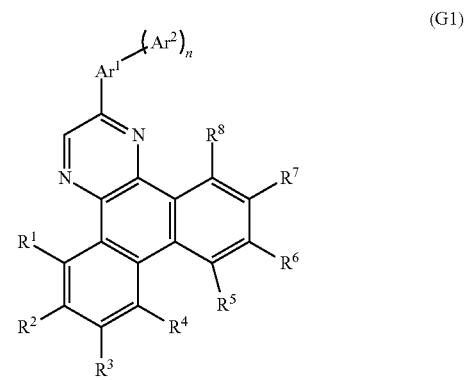

(G1)

In General Formula (G1), $Ar^1$ represents a substituted or unsubstituted arylene group having 6 to 13 carbon atoms; $Ar^2$ represents a substituted or unsubstituted aryl group having 6 to 40 carbon atoms or a substituted or unsubstituted heteroaryl group having 6 to 40 carbon atoms; $R^1$ to $R^8$ separately represent hydrogen, an alkyl group having 1 to 6 carbon atoms, a phenyl group, or a phenyl group having an alkyl group having 1 to 6 carbon atoms as a substituent; and n is any of 1 to 3.

Another embodiment of the present invention is a dibenzo[f,h]quinoxaline derivative that has a chlorine content of 10 ppm or less and obtained by coupling a 2-(chloroaryl)dibenzo[f,h]quinoxaline derivative and an aryl boronic acid or a heteroaryl boronic acid. The 2-(chloroaryl)dibenzo[f,h]quinoxaline derivative is obtained by coupling a 2-chlorodibenzo[f,h]quinoxaline derivative and a chloroaryl boronic acid.

Another embodiment of the present invention is a method of synthesizing a dibenzo[f,h]quinoxaline derivative that includes a step of coupling a 2-(chloroaryl)dibenzo[f,h]quinoxaline derivative and an aryl boronic acid or a heteroaryl boronic acid. The 2-(chloroaryl)dibenzo[f,h]quinoxaline derivative is obtained by coupling a 2-chlorodibenzo[f,h]quinoxaline derivative and a chloroaryl boronic acid.

Another embodiment of the present invention is a light-emitting element that includes any of the above dibenzo[f,h]quinoxaline derivatives.

Another embodiment of the present invention is a light-emitting element that includes a dibenzo[f,h]quinoxaline derivative obtained by the any of the above synthesis method.

Another embodiment of the present invention is a light-emitting element in which an EL layer is provided between a pair of electrodes. In the light-emitting element, the chlorine content of a substance contained as a main component in a light-emitting layer at least included in the EL layer is set to 10 ppm or less, so that the light-emitting element keeps 90% or more of the initial luminance after 200 hours under current with a density of 10 mA/cm$^2$.

Another embodiment of the present invention is a light-emitting element in which an EL layer is provided between a pair of electrodes. In the light-emitting element, the chlorine content of a dibenzo[f,h]quinoxaline derivative used as a main component in a light-emitting layer at least included in the EL layer is set to 10 ppm or less, so that the light-emitting element keeps 90% or more of the initial luminance after 200 hours under current with a density of 10 mA/cm$^2$.

Another embodiment of the present invention is a light-emitting element in which an EL layer is provided between a pair of electrodes. In the light-emitting element, the chlorine content of a dibenzo[f,h]quinoxaline derivative represented by General Formula (G1) used as a main component in a light-emitting layer at least included in the EL layer is set to 10 ppm or less, so that the light-emitting element keeps 90% or more of the initial luminance after 200 hours under current with a density of 10 mA/cm$^2$.

[Chemical Formula 2]

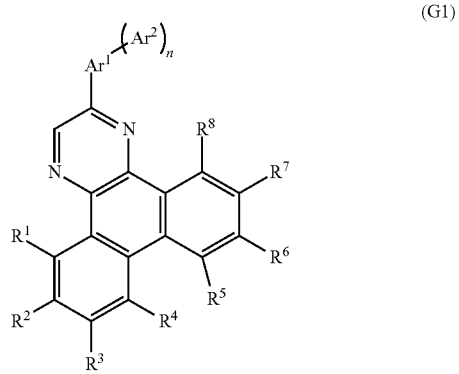

(G1)

In General Formula (G1), Ar$^1$ represents a substituted or unsubstituted arylene group having 6 to 13 carbon atoms; Ar$^2$ represents a substituted or unsubstituted aryl group having 6 to 40 carbon atoms or a substituted or unsubstituted heteroaryl group having 6 to 40 carbon atoms; R$^1$ to R$^8$ separately represent hydrogen, an alkyl group having 1 to 6 carbon atoms, a phenyl group, or a phenyl group having an alkyl group having 1 to 6 carbon atoms as a substituent; and n is any of 1 to 3.

Another embodiment of the present invention is a light-emitting device that includes any of the above-described light-emitting elements.

Note that one embodiment of the present invention includes not only a light-emitting device including the light-emitting element but also an electronic appliance and a lighting device each including the light-emitting device. The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

In one embodiment of the present invention, a dibenzo[f,h]quinoxaline derivative in which impurities are reduced and a method of synthesizing the dibenzo[f,h]quinoxaline derivative can be provided. In one embodiment of the present invention, a light-emitting element, a light-emitting device, an electronic appliance, or a lighting device with high emission efficiency and high reliability in which the dibenzo[f,h]quinoxaline derivative is used as an EL material can be provided. In one embodiment of the present invention, a novel material can be provided. In one embodiment of the present invention, a novel light-emitting element or a novel light-emitting device can be provided. Note that the description of these effects does not disturb the existence of other effects. One embodiment of the present invention does not necessarily achieve all the objects listed above. Other effects will be apparent from and can be derived from the description of the specification, the drawings, the claims, and the like.

DETAILED DESCRIPTION OF THE INVENTION

Figure 1:
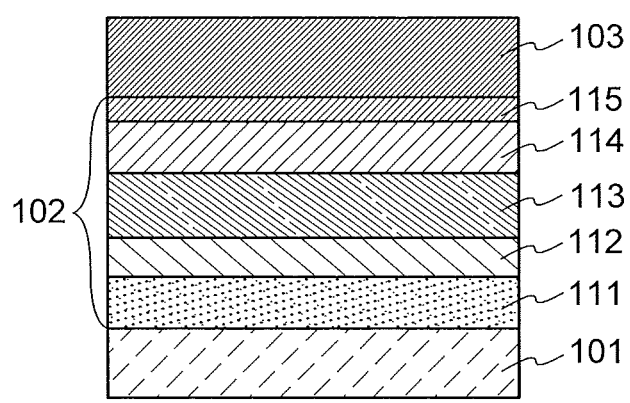
FIG. 1 illustrates a structure of a light-emitting element.

Hereinafter, embodiments of the present invention will be described with reference to the accompanying drawings. Note that the present invention is not limited to the following description, and various changes and modifications can be made without departing from the spirit and scope of the present invention. Therefore, the present invention should not be construed as being limited to the description in the following embodiments.

Embodiment 1

In this embodiment, a method of synthesizing a dibenzo[f,h]quinoxaline derivative of one embodiment of the present invention is described. Note that the dibenzo[f,h]quinoxaline derivative includes a 2-aryl dibenzo[f,h]quinoxaline derivative or a 2-heteroaryl dibenzo[f,h]quinoxaline derivative.

One embodiment of the present invention is a method of synthesizing a dibenzo[f,h]quinoxaline derivative in which impurities are reduced. In this method, 2-(chloroaryl)dibenzo[f,h]quinoxaline derivative is used as a synthetic intermediate in a synthetic pathway so that an impurity contained in a final product can be removed easily by purification by sublimation.

A 2-(chloroaryl)dibenzo[f,h]quinoxaline derivative represented by General Formula (G0) can be synthesized by, for example, Synthesis Scheme (A-1). In other words, as shown in Synthesis Scheme (A-1), a 2-chlorodibenzo[f,h]quinoxaline derivative (General Formula (A1)) is made to react with a chloroaryl boronic acid (General Formula (A2)), whereby the 2-(chloroaryl)dibenzo[f,h]quinoxaline derivative is obtained.

[Chemical Formula 3]

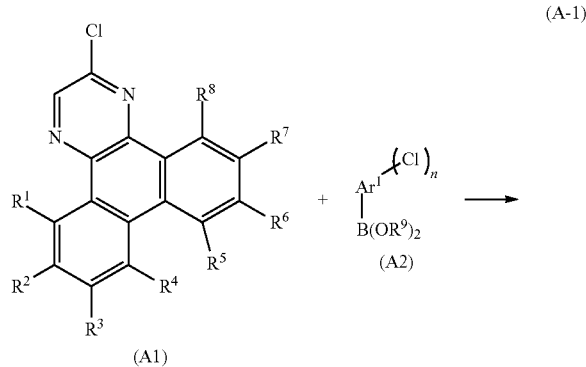

(A-1)

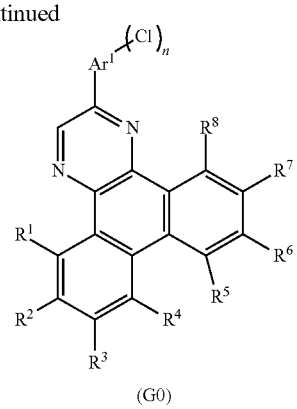

(G0)

In Synthesis Scheme (A-1), $Ar^1$ represents a substituted or unsubstituted arylene group having 6 to 13 carbon atoms; $R^1$ to $R^8$ separately represent hydrogen, an alkyl group having 1 to 6 carbon atoms, a phenyl group, or a phenyl group having an alkyl group having 1 to 6 carbon atoms as a substituent; n is any of 1 to 3; and $R^9$ represents hydrogen or an alkyl group. Note that $R^9$ may be bonded to form a ring structure. For example, a dialkoxyboryl group such as a pinacolboryl group may be used.

In Synthesis Scheme (A-1), the 2-chlorodibenzo[f,h]quinoxaline derivative (General Formula (A1)) that is a source material is generally likely to contain a chlorinated (monochlorinated or dichlorinated) 2-chlorodibenzo[f,h]quinoxaline derivative (e.g., General Formula (A1')) as an impurity. Thus, a chlorinated (monochlorinated or dichlorinated) 2-(chloroaryl)dibenzo[f,h]quinoxaline derivative (i.e., an impurity represented by, for example, General Formula (G0') in which the 2-(chloroaryl)dibenzo[f,h]quinoxaline derivative represented by General Formula (G0) is partly substituted by a plurality of chlorine atoms) can be obtained. However, in the method of synthesizing a dibenzo[f,h]quinoxaline derivative described in this embodiment, a dechlorination reaction in which a chlorine atom is replaced by a hydrogen atom is likely to occur in a chlorinated (monochlorinated or dichlorinated) 2-chlorodibenzo[f,h]quinoxaline derivative (i.e., an impurity represented by, for example, General Formula (A1') in which the 2-chlorodibenzo[f,h]quinoxaline derivative represented by General Formula (A1) is partly substituted by a plurality of chlorine atoms) or a chlorinated (monochlorinated or dichlorinated) 2-(chloroaryl)dibenzo[f,h]quinoxaline derivative (i.e., an impurity represented by, for example, General Formula (G0') in which the 2-(chloroaryl)dibenzo[f,h]quinoxaline derivative represented by General Formula (G0) is partly substituted by a plurality of chlorine atoms), which can exist in the reaction system, while yield of an objective substance by the reaction is kept. Thus, generation of an impurity such as the impurity represented by General Formula (G0') can be suppressed. Note that the dechlorination reaction can be accelerated by increasing the solubility of the 2-(chloroaryl)dibenzo[f,h]quinoxaline derivative represented by General Formula (G0) and decreasing the steric hindrance of $Ar^1$. Thus, $Ar^1$ in Synthesis Scheme (A-1) is preferably a substituted or unsubstituted phenyl group.

[Chemical Formulae 4]

(A1')

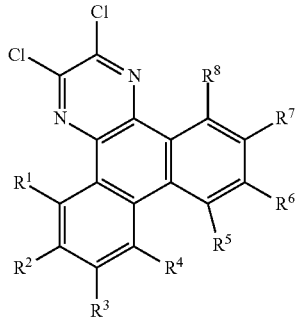

(G0')

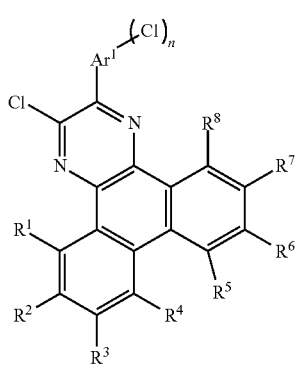

Next, as shown in Synthesis Scheme (A-2), the 2-(chloroaryl)dibenzo[f,h]quinoxaline derivative (General Formula (G0)) and an aryl boronic acid or a heteroaryl boronic acid (General Formula (A3)) are coupled, whereby a dibenzo[f,h]quinoxaline derivative (General Formula (G1)) that has an aryl group or a heteroaryl group as a substituent is synthesized.

[Chemical Formula 5]

(A-2)

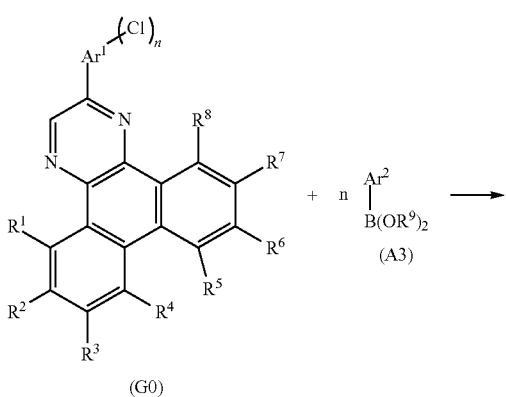

(G1)

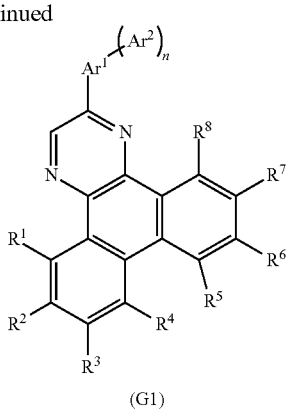

In Synthesis Scheme (A-2), $Ar^1$ represents a substituted or unsubstituted arylene group having 6 to 13 carbon atoms; $Ar^2$ represents a substituted or unsubstituted aryl group having 6 to 40 carbon atoms or a substituted or unsubstituted heteroaryl group having 6 to 40 carbon atoms; $R^1$ to $R^8$ separately represent hydrogen, an alkyl group having 1 to 6 carbon atoms, a phenyl group, or a phenyl group having an alkyl group having 1 to 6 carbon atoms as a substituent; n is any of 1 to 3; and $R^9$ represents hydrogen or an alkyl group. Note that $R^9$ may be bonded to form a ring structure. For example, a dialkoxyboryl group such as a pinacolboryl group may be used.

As described above, the 2-(chloroaryl)dibenzo[f,h]quinoxaline derivative (General Formula (G0)) synthesized by Synthesis Scheme (A-1) has a very small content of impurities represented by, for example, General Formula (G0') in which the 2-(chloroaryl)dibenzo[f,h]quinoxaline derivative represented by General Formula (G0) is partly substituted by a plurality of chlorine atoms. Consequently, in the dibenzo[f,h]quinoxaline derivative (General Formula (G1)) synthesized by Synthesis Scheme (A-2), a chlorinated dibenzo[f,h]quinoxaline derivative (General Formula (G1')) is unlikely to be generated. This leads to a long lifetime of a light-emitting element.

[Chemical Formula 6]

(G1')

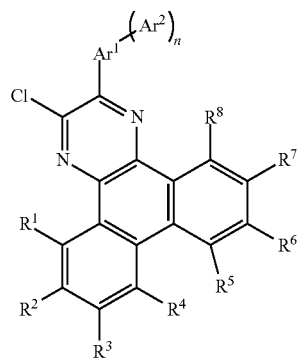

In fact, as described in detail in Example, the dibenzo[f,h]quinoxaline derivative (General Formula (G1)) synthesized by Synthesis Scheme (A-2) has a longer lifetime than a dibenzo[f,h]quinoxaline derivative (General Formula (G1)) synthesized by Synthesis Scheme (B-1).

[Chemical Formulae 7]

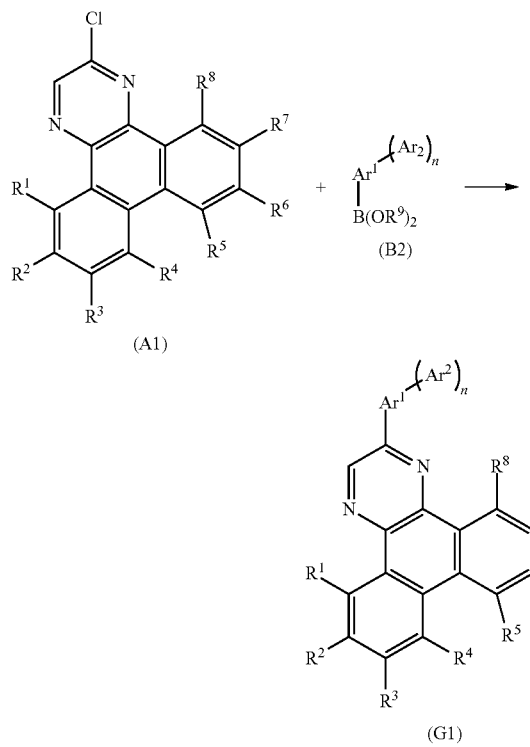

In Synthesis Scheme (B-1), a 2-chlorodibenzo[f,h]quinoxaline derivative (General Formula (A1)) and a boronic acid (General Formula (B2)) having $Ar^1$ and $Ar^2$ which are an aryl group or a heteroaryl group as substituents are coupled, whereby a dibenzo[f,h]quinoxaline derivative (General Formula (G1)) is synthesized. The symbols in Synthesis Scheme (B-1) are the same as those in Synthesis Scheme (A-2).

In that case, the 2-chlorodibenzo[f,h]quinoxaline derivative (General Formula (A1)) that is a source material is generally likely to contain a chlorinated (monochlorinated or dichlorinated) 2-chlorodibenzo[f,h]quinoxaline derivative (General Formula (A1')) as an impurity, which makes separation and purification difficult.

[Chemical Formula 8]

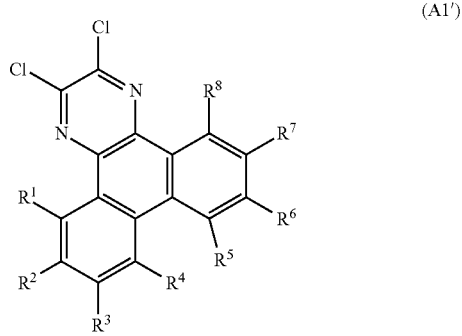

When a reaction shown in Synthesis Scheme (B-1) is performed using the 2-chlorodibenzo[f,h]quinoxaline derivative (General Formula (A1)) containing a chlorinated (monochlorinated or dichlorinated) 2-chlorodibenzo[f,h]quinoxaline derivative (General Formula (A1')), chlorine that is not terminated with a boronic acid (General Formula (B2)) remains as shown in Synthesis Scheme (B-1'). Consequently, a chlorinated dibenzo[f,h]quinoxaline derivative, which is represented by General Formula (G1'), is generated. This has a significant adverse effect on the reliability of a light-emitting element.

[Chemical Formulae 9]

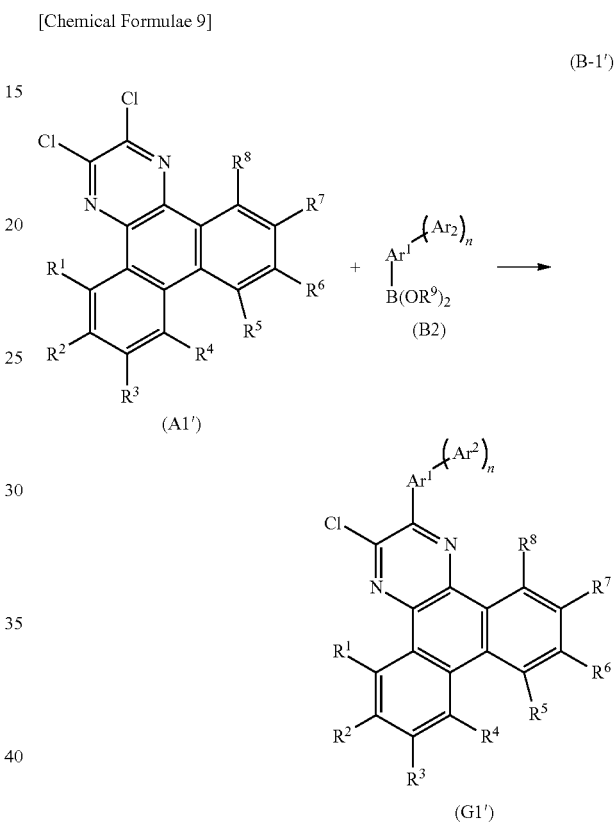

Generation of the chlorinated dibenzo[f,h]quinoxaline derivative (General Formula (G1')) can be suppressed and an adverse effect attributed to the chlorinated dibenzo[f,h]quinoxaline derivative (General Formula (G1')) can be avoided as long as it is possible to terminate all chlorine atoms of the chlorinated 2-chlorodibenzo[f,h]quinoxaline derivative, which is represented by General Formula (A1'), with a boronic acid (General Formula (B2)) in the reaction in Synthesis Scheme (B-1').

However, in the case where chlorine atoms are bonded to the respective adjacent carbon atoms (specifically, the 2-position and the 3-position of pyrazine) in the chlorinated (monochlorinated or dichlorinated) 2-chlorodibenzo[f,h]quinoxaline derivative, which is represented by General Formula (A1'), steric hindrance is large; thus, it is difficult to terminate all of the chlorine atoms with the aryl boronic acid (General Formula (B2)). In other words, in the case where the chlorinated (monochlorinated or dichlorinated) 2-chlorodibenzo[f,h]quinoxaline derivative represented by General Formula (A1') exists, it is difficult to suppress generation of the chlorinated dibenzo[f,h]quinoxaline derivative, which is represented by General Formula (G1').

In addition, the property of the chlorinated dibenzo[f,h] quinoxaline derivative (General Formula (G1')) is similar to that of the dibenzo[f,h]quinoxaline derivative (General Formula (G1)); thus, the chlorinated dibenzo[f,h]quinoxaline derivative is difficult to separate once generated. Particularly in the case where $R^1$ and $R^2$ each represent a phenyl group and the phenyl groups are bonded to each other at the ortho position to form a dibenzo[f,h]quinoxaline ring, the solubility is low and the separation is difficult.

Thus, the synthesis method of one embodiment of the present invention that can suppress generation of the chlorinated dibenzo[f,h]quinoxaline derivative (General Formula (G1')), which is shown in Synthesis Scheme (A-1) and Synthesis Scheme (A-2), enables synthesis of a dibenzo[f,h]quinoxaline derivative in which impurities are reduced.

Note that the 2-(chloroaryl)dibenzo[f,h]quinoxaline derivative (General Formula (G0)) is a useful novel compound and one embodiment of the present invention. Since many kinds of the compounds (General Formula (A1) and General Formula (A2)) used in Synthesis Scheme (A-1) are commercially available or can be synthesized, many kinds of the 2-(chloroaryl)dibenzo[f,h]quinoxaline derivative (General Formula (G0)) can be synthesized by the above synthesis method. Shown below are specific structural formulae of the 2-(chloroaryl)dibenzo[f,h]quinoxaline derivative represented by General Formula (G0) (Structural Formulae (100) to (116)). Note that one embodiment of the present invention is not limited thereto.

[Chemical Formulae 10]

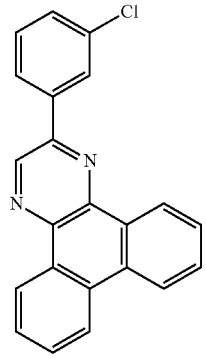
(100)

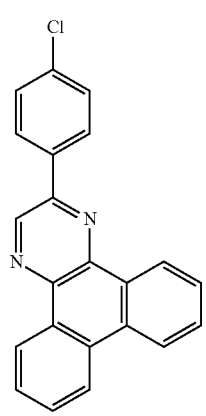
(101)

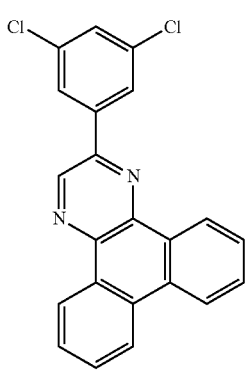
(102)

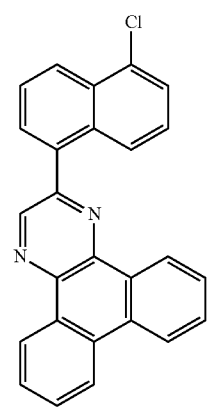
(103)

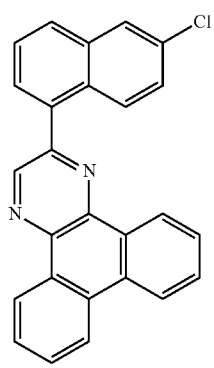
(104)

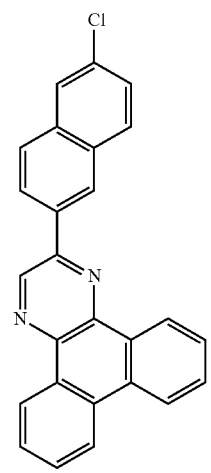
(105)

(106) 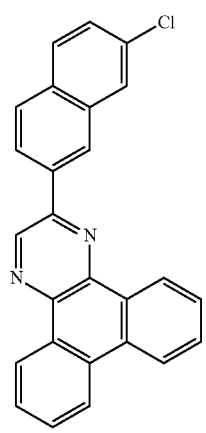
(107) 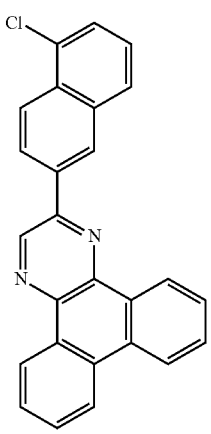
(108) 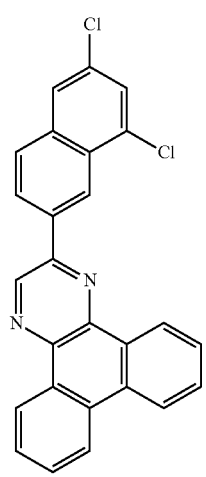
(109) 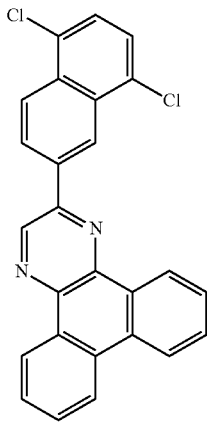
(110) 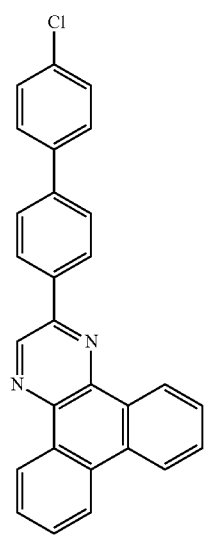
(111) 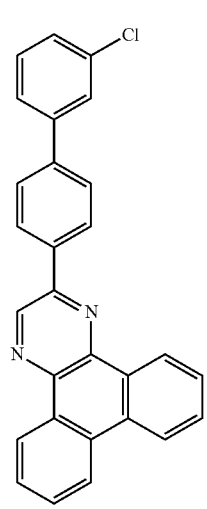

-continued

[Chemical Formulae 11]

(112)

(113)

(114)

-continued (115)

(116)

Shown below are specific structural formulae (Structural Formulae (200) to (213)) of the dibenzo[f,h]quinoxaline derivative (General Formula (G1)) that is obtained by using the 2-(chloroaryl)dibenzo[f,h]quinoxaline derivative (General Formula (G0)) as an intermediate in the synthesis method of one embodiment of the present invention. Note that one embodiment of the present invention is not limited thereto.

[Chemical Formulae 12]

(200)

(201)
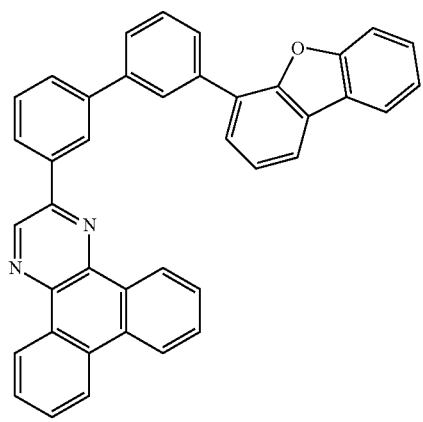
(202)
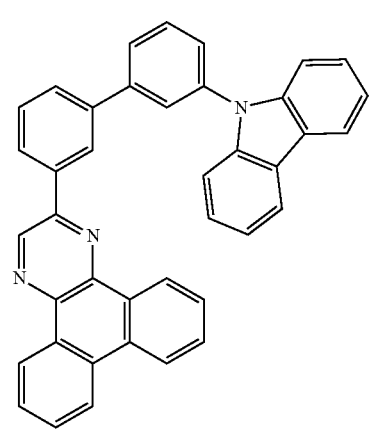
(203)
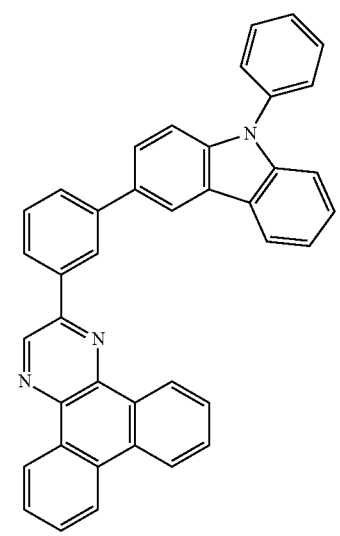
(204)
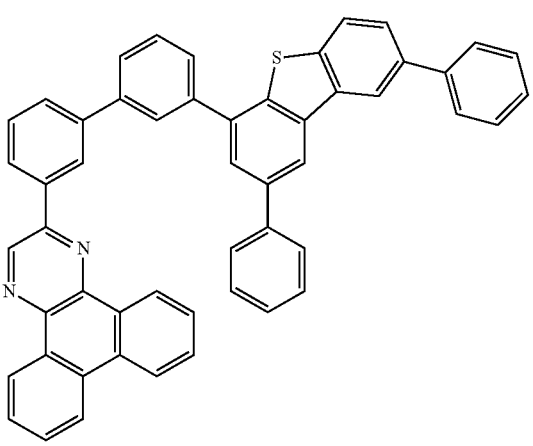
(205)
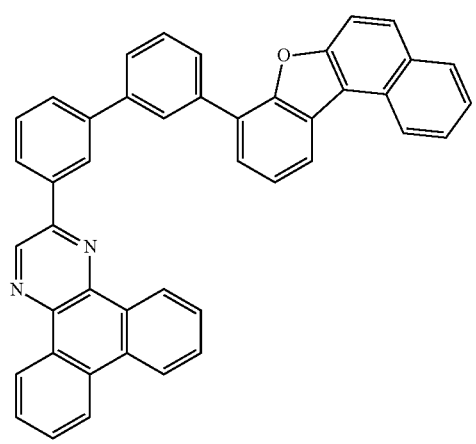
(206)
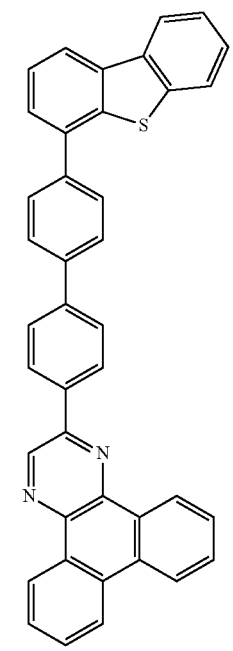

(207)
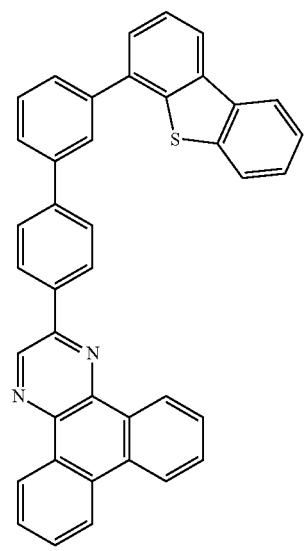
(208)
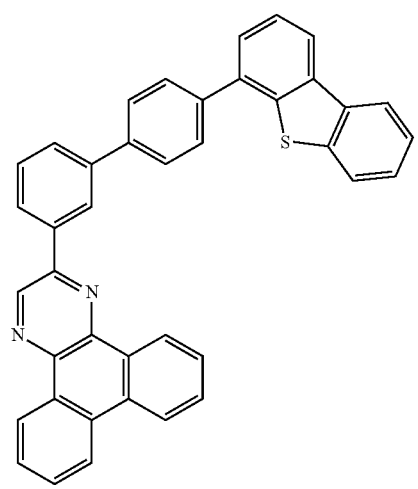
[Chemical Formulae 13]
(209)
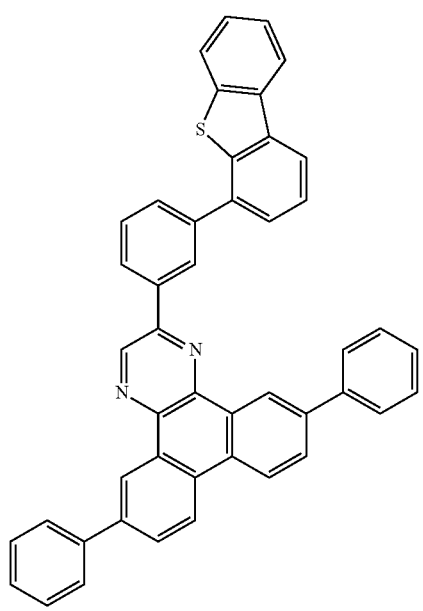
(210)
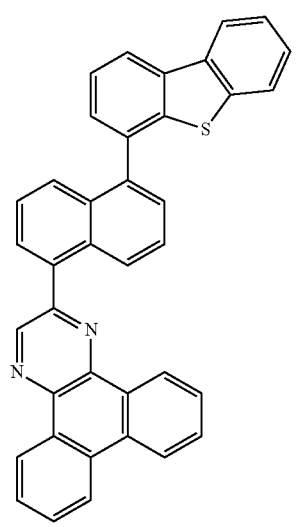
(211)
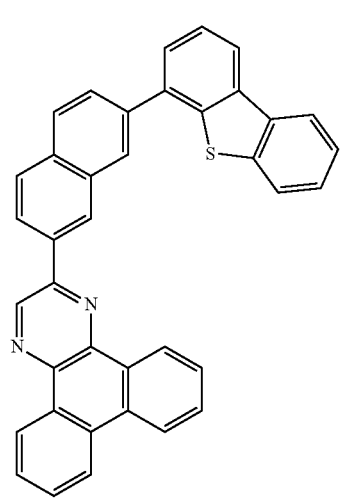
(212)
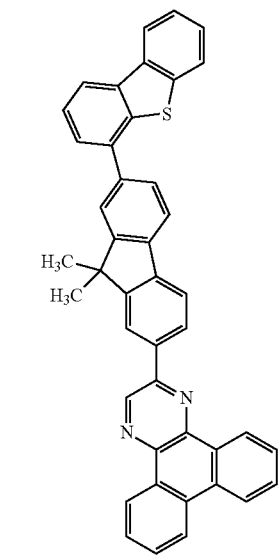

(213)

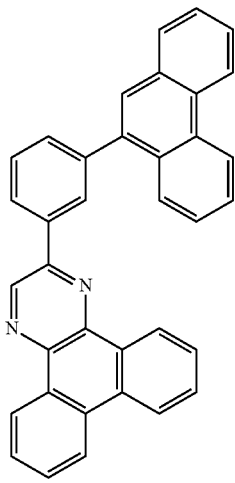

Note that the molecular weight of the dibenzo[f,h]quinoxaline derivative (General Formula (G1)), which is synthesized by the synthesis method of one embodiment of the present invention, is preferably greater than or equal to 400 and less than or equal to 2000. In the case where the molecular weight is less than 400, film quality is poor because of crystallization or the like in fabrication of a light-emitting element, which adversely affects the reliability of the light-emitting element. In the case where the molecular weight is greater than 2000, it is difficult to perform purification by sublimation or vacuum evaporation.

In the method of synthesizing the dibenzo[f,h]quinoxaline derivative of one embodiment of the present invention, which is described above, the 2-(chloroaryl)dibenzo[f,h]quinoxaline derivative is generated as a synthetic intermediate so that an impurity contained in a final product can be removed easily by purification by sublimation.

In other words, a dibenzo[f,h]quinoxaline derivative obtained by the synthesis method of one embodiment of the present invention described above (i.e., a dibenzo[f,h]quinoxaline derivative in which an aryl group is bonded at the 2-position of a dibenzo[f,h]quinoxaline skeleton and the aryl group has at least one aryl group or heteroaryl group as a substituent) can have a chlorine content of 10 ppm or less.

Note that the synthesis method of one embodiment of the present invention enables synthesis of a dibenzo[f,h]quinoxaline derivative in which impurities are reduced; thus, by using the synthesized dibenzo[f,h]quinoxaline derivative as an EL material, a light-emitting element, a light-emitting device, an electronic appliance, or a lighting device with high emission efficiency and high reliability can be obtained. A light-emitting element, a light-emitting device, an electronic appliance, or a lighting device with low power consumption can also be obtained.

Note that the structure described in this embodiment can be combined as appropriate with any of the structures described in the other embodiments.

Embodiment 2

In this embodiment, a light-emitting element in which the dibenzo[f,h]quinoxaline derivative obtained by the synthesis method of one embodiment of the present invention can be used as an EL material is described with reference to FIG. 1. In the dibenzo[f,h]quinoxaline derivative, an aryl group is bonded at the 2-position of a dibenzo[f,h]quinoxaline skeleton and the aryl group has at least one aryl group or heteroaryl group as a substituent.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When voltage is applied to such a light-emitting element, holes injected from the first electrode 101 side and electrons injected from the second electrode 103 side recombine in the light-emitting layer 113 to raise a light-emitting substance contained in the light-emitting layer 113 to an excited state. The light-emitting substance in the excited state emits light when it returns to the ground state.

Although the dibenzo[f,h]quinoxaline derivative synthesized by the synthesis method of one embodiment of the present invention can be used for any one or more layers in the EL layer 102 described in this embodiment, the dibenzo[f,h]quinoxaline derivative is preferably used for the light-emitting layer 113, the hole-transport layer 112, or the electron-transport layer 114. In other words, the dibenzo[f,h]quinoxaline derivative is used in part of a light-emitting element having a structure described below.

In particular, by using the dibenzo[f,h]quinoxaline derivative obtained by the synthesis method of one embodiment of the present invention for a light-emitting layer, the chlorine content of a substance contained as a main component in the light-emitting layer can be 10 ppm or less. Consequently, it is possible to fabricate a light-emitting element that keeps 90% or more of the initial luminance after 200 hours under current with a density of 10 mA/cm$^2$.

In other words, the light-emitting element of one embodiment of the present invention is a light-emitting element in which an EL layer is provided between a pair of electrodes and the chlorine content of a dibenzo[f,h]quinoxaline derivative used as a main component in a light-emitting layer at least included in the EL layer is set to 10 ppm or less, so that the light-emitting element keeps 90% or more of the initial luminance after 200 hours under current with a density of 10 mA/cm$^2$.

In addition, the light-emitting element of one embodiment of the present invention is a light-emitting element in which an EL layer is provided between a pair of electrodes and the chlorine content of a dibenzo[f,h]quinoxaline derivative represented by General Formula G1 used as a main component in a light-emitting layer at least included in the EL layer is set to 10 ppm or less, so that the light-emitting element keeps 90% or more of the initial luminance after 200 hours under current with a density of 10 mA/cm$^2$.

A specific example in which the light-emitting element described in this embodiment is fabricated is described below.

As the first electrode (anode) 101 and the second electrode (cathode) 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

The hole-injection layer 111 injects holes into the light-emitting layer 113 through the hole-transport layer 112 with a high hole-transport property. The hole-injection layer 111 contains a substance with a high hole-transport property and an acceptor substance, so that electrons are extracted from the substance with a high hole-transport property by the acceptor substance to generate holes and the holes are injected into the light-emitting layer 113 through the hole-transport layer 112. The hole-transport layer 112 is formed using a substance with a high hole-transport property.

Specific examples of the substance with a hole-transport property, which is used for the hole-injection layer 111 and the hole-transport layer 112, include aromatic amine compounds such as 4,4'-bis[N-(1-naphthyl)-N-phenylamino]biphenyl (abbreviation: NPB or a-NPD), N,N'-bis(3-methylphenyl)-N,N-diphenyl[1,1'biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $10^{-6}$ cm$^2$/Vs or higher. Note that any substance other than the substances listed here may be used as long as the hole-transport property is higher than the electron-transport property.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the acceptor substance that is used for the hole-injection layer 111 include transition metal oxides and oxides of metals belonging to Groups 4 to 8 of the periodic table. Specifically, molybdenum oxide is particularly preferable.

The light-emitting layer 113 is a layer containing a light-emitting substance. The light-emitting layer 113 may contain only a light-emitting substance; alternatively, an emission center substance (guest material) may be dispersed in a host material in the light-emitting layer 113. Note that a substance that has high triplet excitation energy is preferably used as the host material.

There is no particular limitation on the material that can be used as the light-emitting substance and the emission center substance in the light-emitting layer 113. A light-emitting substance converting singlet excitation energy into luminescence (hereinafter, referred to as fluorescent substance) or a light-emitting substance converting triplet excitation energy into luminescence (hereinafter, referred to as phosphorescent substance) can be used. Examples of the light-emitting substance and the emission center substance are given below.

As an example of the light-emitting substance converting singlet excitation energy into luminescence, a substance emitting fluorescence can be given.

Examples of the substance emitting fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DUJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into luminescence include a substance emitting phosphorescence and a thermally activated delayed fluorescence (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance emitting phosphorescence include bis{2-[3',5'-bis(trifluoromethyl)phenyl]pyridinato-N,$C^{2'}$}iridium(III) picolinate (abbreviation: Ir(CF$_3$ppy)$_2$(pic)), bis[2-(4',6'-difluorophenyl)pyridinato-N,$C^{2'}$]iridium (III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium (III) acetylacetonate (abbreviation: Ir(bt)$_2$(acac)), bis[2-(2'-benzo[4,5-a]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrinplatinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

Preferable examples of the substance (i.e., host material) used for dispersing the light-emitting substance converting triplet excitation energy into luminescence include compounds having an arylamine skeleton, such as 2,3-bis(4-diphenylaminophenyl)quinoxaline (abbreviation: TPAQn) and NPB, carbazole derivatives such as CBP and 4,4',4''-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolato)(4-phenylphenolato)aluminum (abbreviation: BAlq), and tris(8-quinolinolato)aluminum (abbreviation: Alq$_3$). Alternatively, a high molecular compound such as PVK can be used.

Examples of the TADF material includes fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (PIC-TRZ). Note that a material in which the π-electron rich heteroaromatic ring is directly bonded to the π-electron deficient heteroaromatic ring is particularly preferably used because both the donor property of the π-electron rich heteroaromatic ring and the acceptor property of the π-electron deficient heteroaromatic ring are increased and the energy difference between the $S_1$ level and the $T_1$ level becomes small.

When a host material and any of the light-emitting substances converting singlet excitation energy into luminescence or any of the light-emitting substances converting triplet excitation energy into luminescence (i.e., a guest material) are contained in the light-emitting layer 113, light emission with high emission efficiency can be obtained from the light-emitting layer 113.

The electron-transport layer 114 is a layer containing a substance with a high electron-transport property. For the electron-transport layer 114, a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used. heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1 \times 10^{-6}$ cm$^2$/Vs or higher. Note that any substance other than the substances listed here may be used for the electron-transport layer 114 as long as the electron-transport property is higher than the hole-transport property.

The electron-transport layer 114 is not limited to a single layer, but may be a stack of two or more layers each containing any of the substances listed above.

The electron-injection layer 115 is a layer containing a substance with a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specific examples are an alkali metal, an alkaline earth metal, and a rare earth metal are preferable, and lithium, cesium, magnesium, calcium, erbium, and ytterbium. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, current flows because of a potential difference generated between the first electrode 101 and the second electrode 103 and holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

Note that the light-emitting element described in this embodiment is an example of a light-emitting element in which the dibenzo[f,h]quinoxaline derivative obtained by the synthesis method of one embodiment of the present invention is used as an EL material. As a light-emitting device including the above-described light-emitting element, a passive matrix light-emitting device and an active matrix light-emitting device can be fabricated. It is also possible to fabricate a light-emitting device including a light-emitting element having a microcavity structure. Each of the light-emitting devices is one embodiment of the present invention.

Note that there is no particular limitation on the structure of the transistor (FET) in the case of fabricating the active matrix light-emitting device. For example, a staggered FET or an inverted staggered FET can be used as appropriate. A driver circuit formed over a FET substrate may be formed of both an n-type FET and a p-type FET or only either an n-type FET or a p-type FET. Furthermore, there is no particular limitation on the crystallinity of a semiconductor film used for the FET. For example, either an amorphous semiconductor film or a crystalline semiconductor film can be used. Examples of a semiconductor material include Group IV semiconductors (e.g., silicon), Group III semiconductors (e.g., gallium), compound semiconductors (including oxide semiconductors), and organic semiconductors.

Note that the structure described in this embodiment can be combined as appropriate with any of the structures described in the other embodiments.

Embodiment 3

Described in this embodiment is a case of fabricating a light-emitting element (hereinafter, a tandem light-emitting element) that has a structure in which a charge-generation layer is provided between a plurality of EL layers and the dibenzo[f,h]quinoxaline derivative obtained by the synthesis method of one embodiment of the present invention is used as an EL material in the EL layers.

Figure 2A:
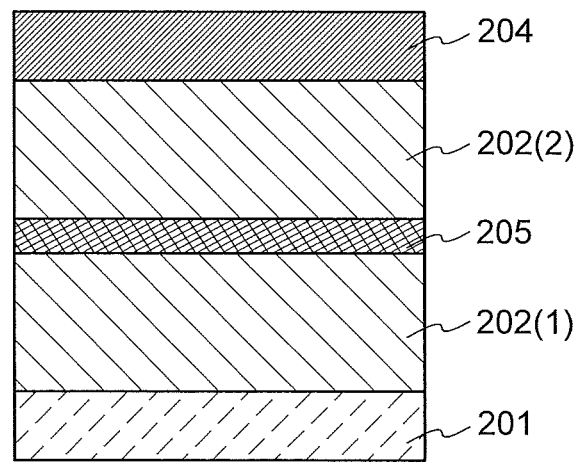
FIGS. 2A and 2B each illustrate a structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204) as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, all or any of the plurality of EL layers (the first EL layer 202(1) and the second EL layer 202(2)) may have structures similar to those described in Embodiment 2. In other words, the structures of the first EL layer 202(1) and the second EL layer 202(2) may be the same or different from each other and can be similar to those of the EL layers described in Embodiment 2.

In addition, a charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer (I) 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances listed here are mainly ones that have a hole mobility of $10^{-6}$ cm$^2$/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Transition metal oxides can also be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, Bphen, BCP, or the like can be used. The substances listed here are mainly ones that have an electron mobility of $10^{-6}$ cm$^2$/Vs or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers.

Figure 2B:
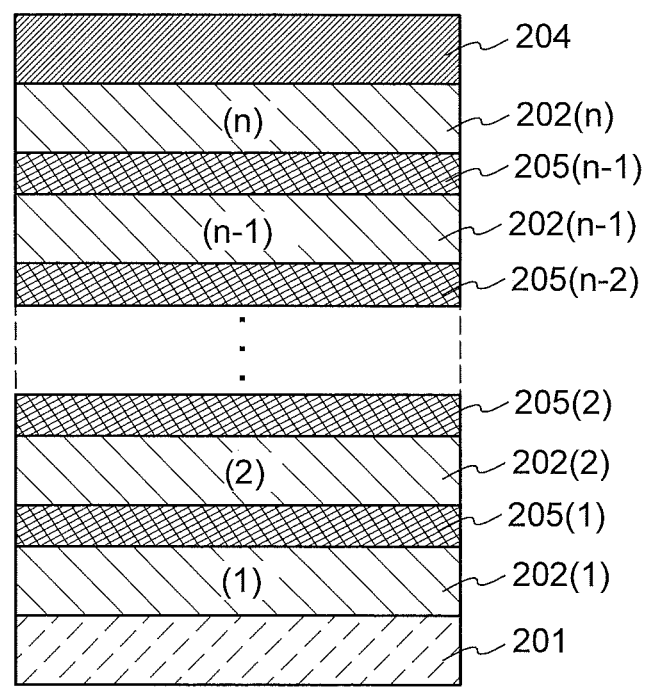

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, which results in homogeneous light emission in a large area. In addition, a low-power-consumption light-emitting device that can be driven at low voltage can be achieved.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that "complementary colors" refer to colors that can produce an achromatic color when mixed. In other words, emission of white light can be obtained by mixture of light emitted from substances whose emission colors are complementary colors.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

Described in this embodiment is a light-emitting device that includes a light-emitting element in which the dibenzo[f,h]quinoxaline derivative obtained by the synthesis method of one embodiment of the present invention is used as an EL material in a light-emitting layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Figure 3A:
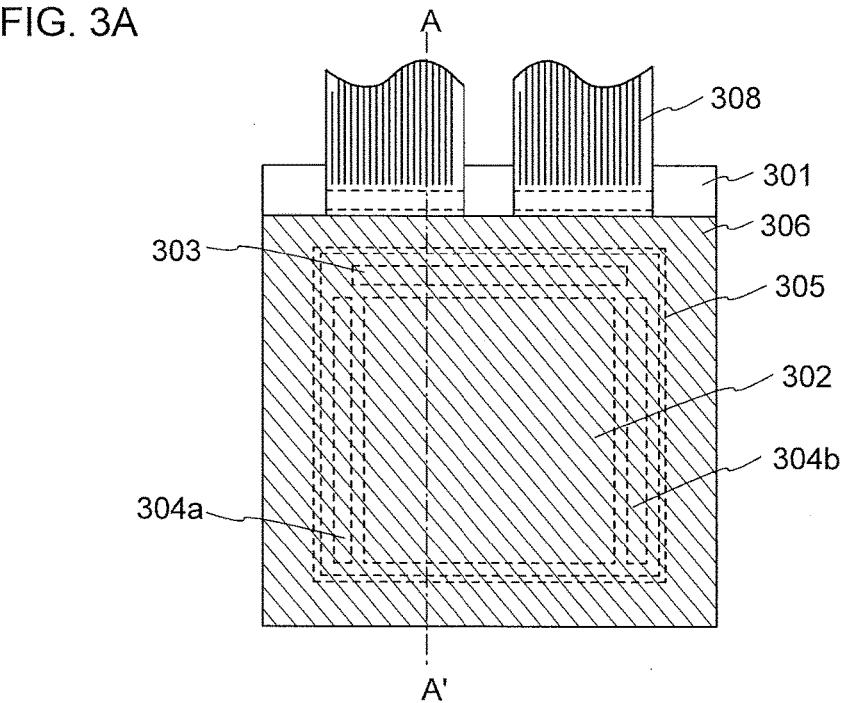
FIGS. 3A and 3B illustrate a light-emitting device.
Figure 3B:
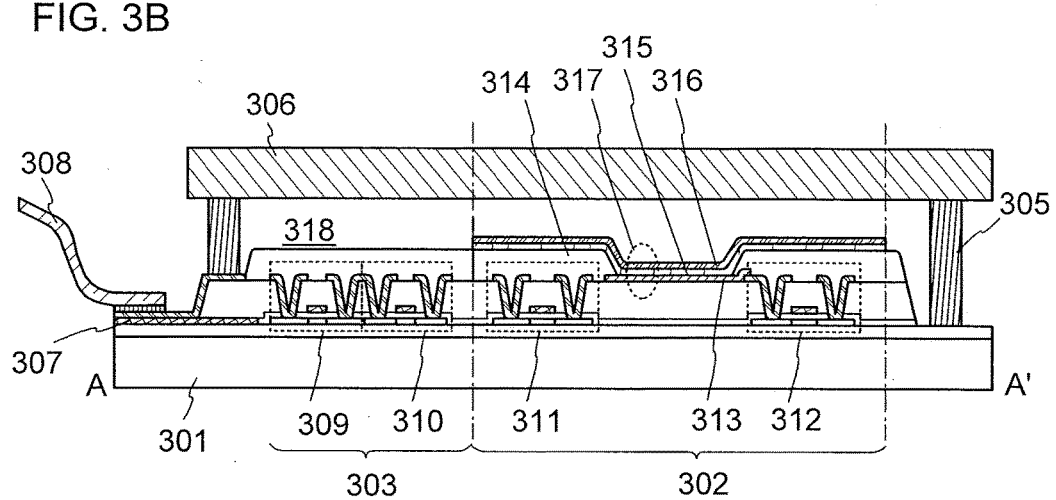

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either an n-channel transistor or a p-channel transistor) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 that is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. Examples of a semiconductor material that can be used for the FETs 309, 310, 311, and 312 include Group IV semiconductors (e.g., silicon), Group III semiconductors (e.g., gallium), compound semiconductors, oxide semiconductors, and organic semiconductors. In addition, there is no particular limitation on the crystallinity of the semiconductor material, and an amorphous semiconductor or a crystalline semiconductor can be used. In particular, an oxide semiconductor is preferably used for the FETs 309, 310, 311, and 312. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 309, 310, 311, and 312, so that the off-state current of the transistors can be reduced.

In addition, an insulator 314 is formed to cover end portions of the first electrode (anode) 313. In this embodiment, the insulator 314 is formed using a positive photosensitive acrylic resin. The first electrode 313 is used as an anode in this embodiment.

The insulator 314 preferably has a curved surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material of the insulator 314 is not limited to an organic compound and an inorganic compound such as silicon oxide, silicon oxynitride, or silicon nitride can also be used.

An EL layer 315 and a second electrode (cathode) 316 are stacked over the first electrode (anode) 313. In the EL layer 315, at least a light-emitting layer is provided. In the EL layer 315, a hole-injection layer, a hole-transport layer, an electron-transport layer, an electron-injection layer, a charge-generation layer, and the like can be provided as appropriate in addition to the light-emitting layer.

A light-emitting element 317 is formed of a stack of the first electrode (anode) 313, the EL layer 315, and the second electrode (cathode) 316. For the first electrode (anode) 313, the EL layer 315, and the second electrode (cathode) 316, any of the materials given in Embodiment 2 can be used. Although not illustrated, the second electrode (cathode) 316 is electrically connected to the FPC 308 which is an external input terminal.

Although the cross-sectional view of FIG. 3B illustrates only one light-emitting element 317, a plurality of light-emitting elements are arranged in matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby effects such as an improvement in color purity and a reduction in power consumption can be obtained. Alternatively, a light-emitting device that is capable of full color display may be fabricated by combination with color filters.

Furthermore, the sealing substrate 306 is attached to the element substrate 301 with the sealant 305, whereby a light-emitting element 317 is provided in a space 318 surrounded by the element substrate 301, the sealing substrate 306, and the sealant 305. Note that the space 318 may be filled with an inert gas (such as nitrogen and argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), polyvinyl fluoride) (PVF), polyester, acrylic, or the like can be used. In the case where glass frit is used as the sealant, the element substrate 301 and the sealing substrate 306 are preferably glass substrates for high adhesion As described above, an active matrix light-emitting device can be obtained.

Note that the structure described in this embodiment can be combined as appropriate with any of the structures described in the other embodiments.

Embodiment 5

In this embodiment, examples of an electronic appliance manufactured using a light-emitting device in which the dibenzo[f,h]quinoxaline derivative obtained by the synthesis method of one embodiment of the present invention is used as an EL material are described with reference to FIGS. 4A to 4D.

Examples of electronic appliances including the light-emitting device include television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, and large game machines such as pachinko machines. Specific examples of the electronic appliances are illustrated in FIGS. 4A to 4D.

Figure 4A:
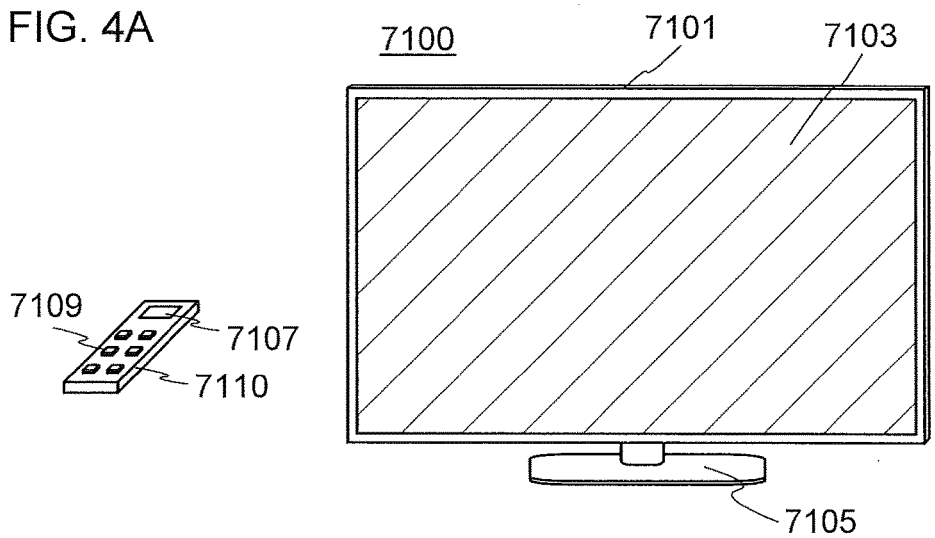
FIGS. 4A to 4D illustrate electronic appliances.

FIG. 4A illustrates an example of a television device. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
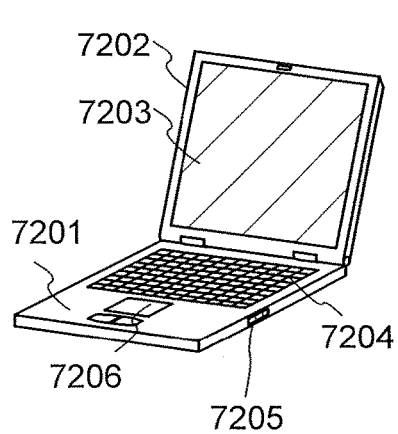

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device for the display portion 7203.

Figure 4C:
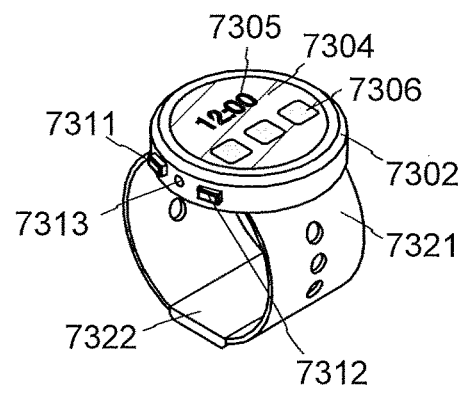

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like.

The smart watch illustrated in FIG. 4C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 4D:
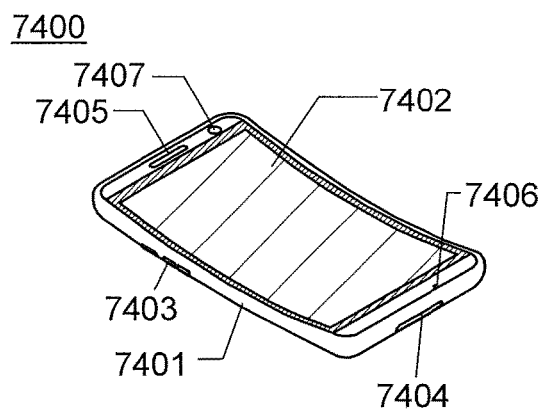

FIG. 4D illustrates an example of a mobile phone. A mobile phone 7400 includes a housing 7401 provided with a display portion 7402, a microphone 7406, a speaker 7405, a camera 7407, an external connection portion 7404, an operation button 7403, and the like. In the case where the light-emitting element of one embodiment of the present invention is formed over a flexible substrate, the light-emitting element can be used for the display portion 7402 having a curved surface as illustrated in FIG. 4D.

When the display portion 7402 of the mobile phone 7400 illustrated in FIG. 4D is touched with a finger or the like, data can be input to the mobile phone 7400. In addition, operations such as making a call and composing an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically changed by determining the orientation of the mobile phone 7400 (whether the mobile phone is placed horizontally or vertically for a landscape mode or a portrait mode).

The screen modes are changed by touch on the display portion 7402 or operation with the button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, when a backlight or a sensing light source that emits near-infrared light is provided in the display portion, an image of a finger vein, a palm vein, or the like can be taken.

As described above, the electronic appliances can be obtained using the light-emitting device that includes the light-emitting element fabricated by the fabrication method of one embodiment of the present invention. Note that the light-emitting device can be used for electronic appliances in a variety of fields without being limited to the electronic appliances described in this embodiment.

Note that the structure described in this embodiment can be combined as appropriate with any of the structures described in the other embodiments.

Embodiment 6

In this embodiment, examples of a lighting device that includes a light-emitting device containing the dibenzo[f,h]quinoxaline derivative obtained by the synthesis method of one embodiment of the present invention are described with reference to FIG. 5.

Figure 5:
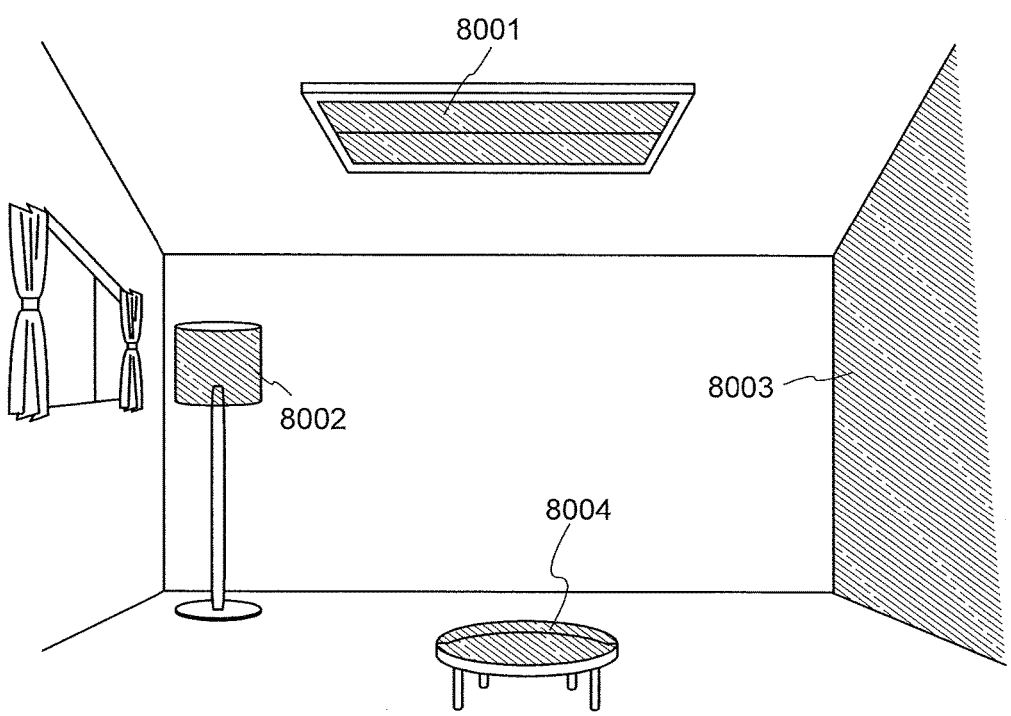
FIG. 5 illustrates lighting devices.

FIG. 5 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Thus, the lighting device can be elaborately designed in a variety of ways. In addition, a wall of the room may be provided with a large-sized lighting device 8003.

When the light-emitting device is used for a table by being used as a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Example 1

Synthesis Example 1

In this example, a method of synthesizing 2-[3'-(dibenzothiophen-4-yl)biphenyl-3-yl]dibenzo[f,h]quinoxaline (abbreviation: 2mDBTBPDBq-II) (Structural Formula (200)) is described as a synthesis method of one embodiment of the present invention. Note that a structure of 2mDBTBPDBq-II is shown below.

[Chemical Formula 14]

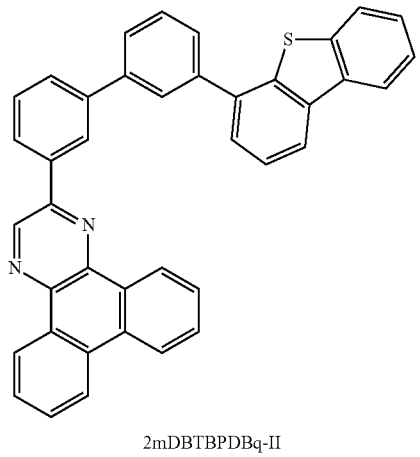

(200)

2mDBTBPDBq-II

Step 1: Synthesis of 2-(3-chlorophenyl)dibenzo[f,h]quinoxaline

First, 19.9 g (75 mmol) of 2-chlorodibenzo[f,h]quinoxaline (Structural Formula (301)), 12.9 g (82.5 mmol) of 3-chlorophenyl boronic acid, 31.1 g (225 mmol) of potassium carbonate, 380 mL of toluene, 100 mL of ethanol, and 115 mL of water were put in a 1-L three-neck flask, and the air in the flask was replaced with nitrogen. This mixture was degassed by being stirred under reduced pressure.

Then, 0.51 g (2.25 mmol) of palladium(II) acetate (abbreviation: Pd(OAc)₂) and 1.53 g (4.5 mmol) of tris(2-methylphenyl)phosphine were added to the mixture. This mixture was stirred at approximately 80° C. under a nitrogen stream for 6 hours to precipitate a gray solid. The gray solid was separated by suction filtration and washed with ethanol, water, and ethanol in this order. The obtained solid was dried at 70° C. under reduced pressure to give 24.3 g of an objective substance in a yield of 95%.

Synthesis Scheme (a-1) of Step 1 is shown below.

[Chemical Formulae 15]

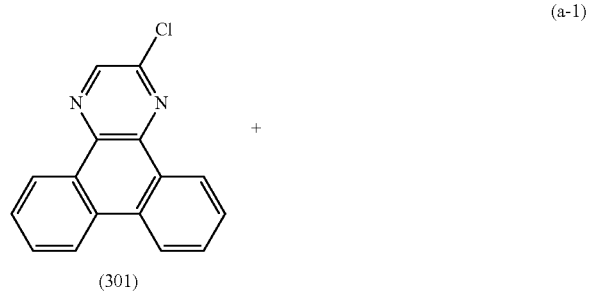

(a-1)

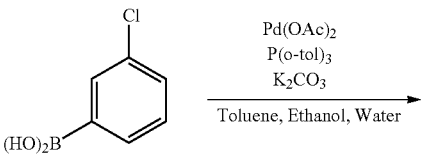

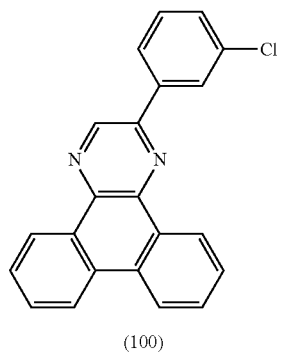

(100)

Figure 6A:
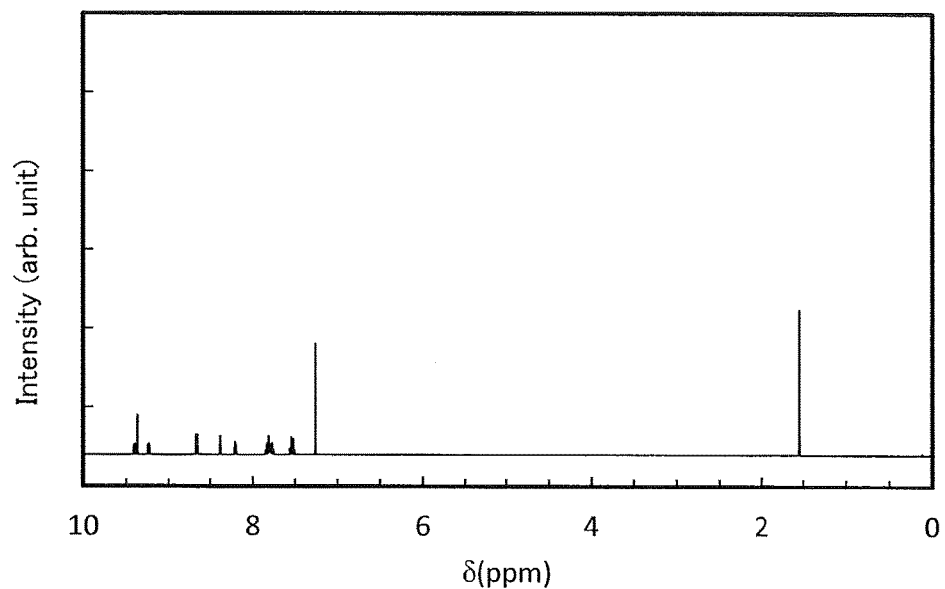
FIGS. 6A and 6B are $^1$H-NMR charts of an intermediate represented by Structural Formula (100).
Figure 6B:
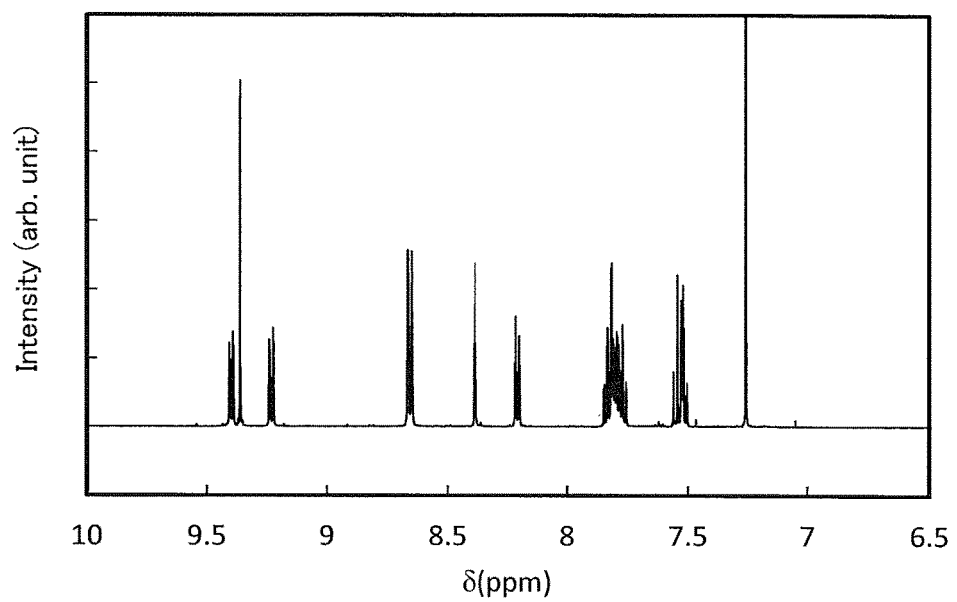

Analysis results by nuclear magnetic resonance (¹H-NMR) spectroscopy of the gray solid obtained in Step 1 are described below. FIGS. 6A and 6B are ¹H-NMR charts. FIG. 6B is a chart where the range from 6.5 (ppm) to 10 (ppm) on the horizontal axis (δ) in FIG. 6A is enlarged. The charts show that 2-(3-chlorophenyl)dibenzo[f,h]quinoxaline (Structural Formula (100)) was obtained in Step 1.

¹H NMR (CDCl₃, 500 MHz): δ (ppm)=7.50-7.57 (m, 2H), 7.74-7.85 (m, 4H), 8.20 (td, J=7.5 Hz, 1.5 Hz, 1H), 8.38 (t, J=2.0 Hz, 1H), 8.66 (d, J=8.0 Hz, 2H), 9.23 (dd, J=8.0 Hz, 2.0 Hz, 1H), 9.36 (s, 1H), 9.40 (dd, J=8.5 Hz, 2.0 Hz, 1H).

Step 2: Synthesis of 2-[3'-(dibenzothiophen-4-yl)biphenyl-3-yl]dibenzo[f,h]quinoxaline (abbreviation: 2mDBTBPDBq-II)

Next, 23.9 g (70 mmol) of 2-(3-chlorophenyl)dibenzo[f,h]quinoxaline obtained in Step 1, 23.4 g (77 mmol) of 3-(dibenzothiophen-4-yl)phenylboronic acid, 44.6 g (210 mmol) of tripotassium phosphate, 15.6 g (210 mmol) of t-butanol, and 470 mL of dioxane were put in a 1-L three-neck flask, and the air in the flask was replaced with nitrogen. This mixture was degassed by being stirred under reduced pressure.

Then, 157 mg (0.70 mmol) of palladium(II) acetate, 502 mg (1.4 mmol) of di(1-adamantyl)-n-butylphosphine (abbreviation: cataCXium®), and 2-(3-chlorophenyl)dibenzo[f,h]quinoxaline were added to the mixture. This mixture was stirred at approximately 100° C. under a nitrogen stream for 14 hours. After reaction, a precipitated gray solid was separated by suction filtration to give a solid. The solid was washed with ethanol, water, ethanol, and toluene in this order. The obtained solid was dried at 100° C. under reduced pressure to give 37.6 g of an objective substance in a yield of 95%.

By a train sublimation method, 35 g of the objective solid, which was the objective substance, was purified. In the purification by sublimation, the objective substance was heated at 325° C. under a pressure of 2.7 Pa. After cooling, 29.6 g of a pale yellow solid was obtained in a yield of 84%. Synthesis Scheme (a-2) of Step 2 is shown below.

[Chemical Formulae 16]

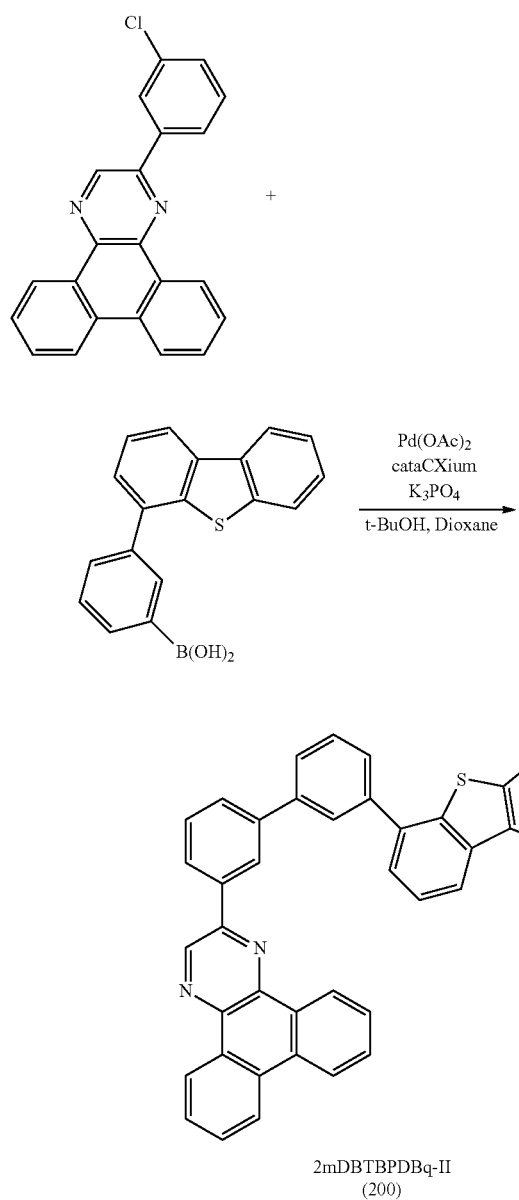

2mDBTBPDBq-II
(200)

Figure 7A:
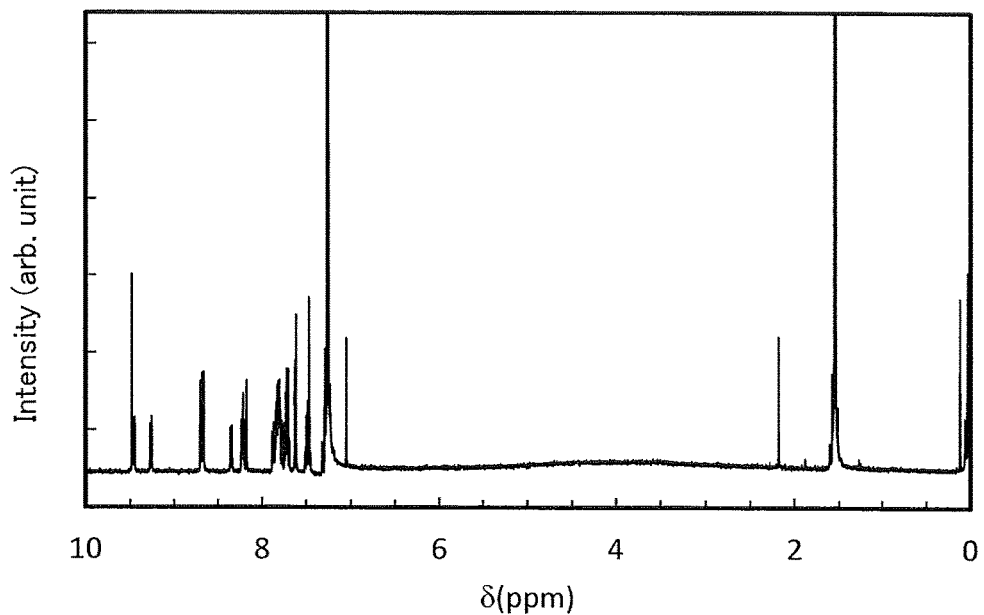
FIGS. 7A and 7B are $^1$H-NMR charts of an EL material represented by Structural Formula (200).
Figure 7B:
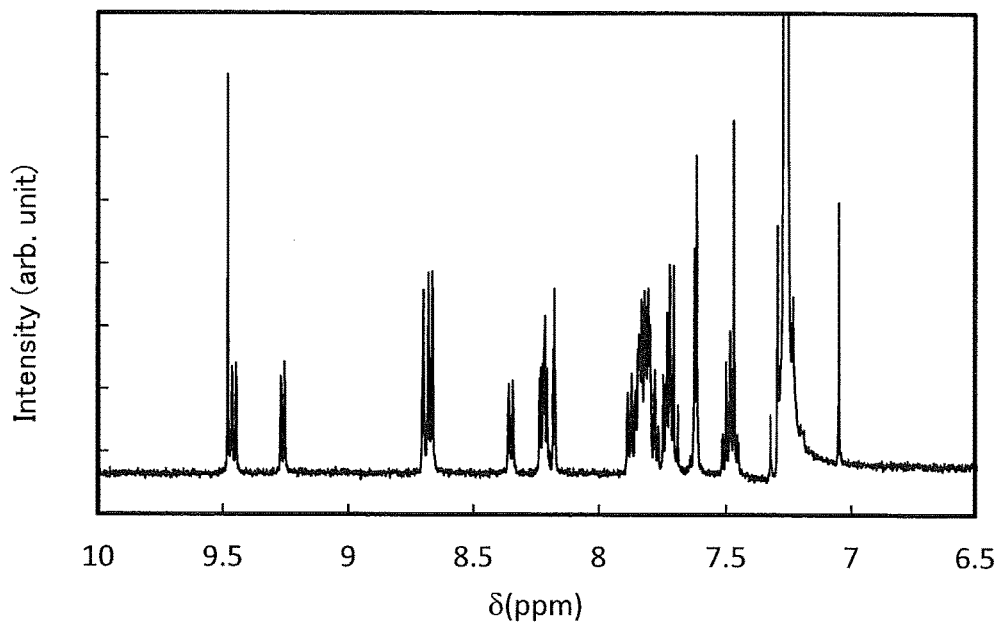

Analysis results by nuclear magnetic resonance (¹H-NMR) spectroscopy of the pale yellow solid obtained in Step 2 are described below. FIGS. 7A and 7B are ¹H-NMR charts. FIG. 7B is a chart where the range from 6.5 (ppm) to 10 (ppm) on the horizontal axis (δ) in FIG. 7A is enlarged. The charts show that 2-[3'-(dibenzothiophen-4-yl)biphenyl-3-yl]dibenzo[f,h]quinoxaline (abbreviation: 2mDBTBP-DBq-II) (Structural Formula (200)) was obtained in Step 1.

¹H NMR (CDCl₃, 500 MHz): δ (ppm)=7.44-7.52 (m, 2H), 7.62 (d, J=5.0 Hz, 2H), 7.68-7.75 (m, 3H), 7.75-7.89 (m, 7H), 8.18 (s, 1H), 8.19-8.24 (m, 2H), 8.35 (d, J=7.0 Hz, 1H), 8.67 (d, J=8.0 Hz, 2H), 8.70 (s, 1H), 9.26 (d, J=7.5 Hz, 1H), 9.45 (d, J=8.0 Hz, 1H), 9.48 (s, 1H).

Here, the purity of 2-chlorodibenzo[f,h]quinoxaline (Structural Formula (301)), which was used as a source material in Step 1, was analyzed by ACQUITY Ultra Performance LC (hereinafter, ACQUITY UPLC). According to the analysis, in addition to 2-chlorodibenzo[f,h]quinoxaline (Structural Formula (301)), substances with m/z (i.e., mass-to-charge ratio) of 231 and 299 were contained as impurities with area ratios of 0.3% and 0.8%, respectively, and the purity was calculated to be 98.7%. The impurities with m/z of 231 and 299 are presumed to be dibenzo[f,h]quinoxaline (Structural Formula (302)) and a monochlorinated 2-chlorodibenzo[f,h]quinoxaline (Structural Formula (303)) shown below, respectively.

[Chemical Formulae 17]

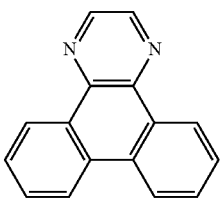
(302)

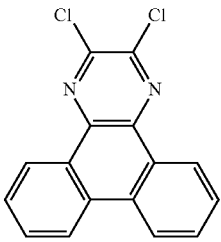
(303)

The above results indicate that the 2-chlorodibenzo[f,h]quinoxaline derivative (General Formula (A1)), which was used as a source material in a synthesis method (Synthesis Scheme (A-1)) in Embodiment 1, generally contains a chlorinated (monochlorinated or dichlorinated) 2-chlorodibenzo[f,h]quinoxaline derivative represented by General Formula (A1') as an impurity.

[Chemical Formula 18]

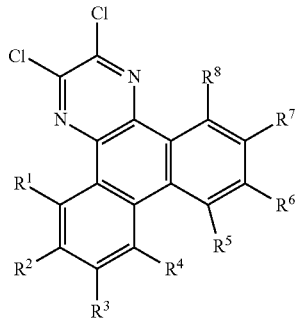
(A1')

Note that in General Formula (A1'), R¹ to R⁸ separately represent hydrogen, an alkyl group having 1 to 6 carbon atoms, a phenyl group, or a phenyl group having an alkyl group having 1 to 6 carbon atoms as a substituent.

Next, the purity of 2-(3-chlorophenyl)dibenzo[f,h]quinoxaline (Structural Formula (100)), which was the compound (i.e., intermediate) obtained in Step 1, was analyzed similarly. According to the analysis, in addition to 2-(3- chlorophenyl)dibenzo[f,h]quinoxaline (Structural Formula (100)), substances with m/z (i.e., mass-to-charge ratio) of 265, 307, 417, and 493 were contained as impurities with area ratios of 0.1%, 0.3%, 0.3%, and 0.1%, respectively, and the purity was calculated to be 99.2%. The impurities with m/z of 265, 307, 417, and 493 are presumed to be 2-chlorodibenzo[f,h]quinoxaline, 2-phenyldibenzo[f,h]quinoxaline, 2-[3-(3'-chlorophenyl)-phenyl]dibenzo[f,h]quinoxaline, and 2-{3-[3'-(3''-chlorophenyl)-phenyl]phenyl}dibenzo[f,h]quinoxaline, respectively. Note that these impurities are consumed in subsequent reaction or can be removed by purification. In addition, the results of the purity analysis indicate that an impurity (i.e., a chloride (a monochloride or a dichloride)) originating from the monochlorinated 2-chlorodibenzo[f,h]quinoxaline (Structural Formula (303)), which is an impurity that can be contained in the source material, i.e., 2-chlorodibenzo[f,h]quinoxaline (Structural Formula (301)), is hardly detected in the synthesis method.

Even when the 2-chlorodibenzo[f,h]quinoxaline derivative (General Formula (A1)), which is used as a source material, contains a chlorinated (monochlorinated or dichlorinated) 2-chlorodibenzo[f,h]quinoxaline derivative represented by General Formula (A1') as an impurity in the synthesis method (Synthesis Scheme (A-1)) described in Embodiment 1, a substance produced in addition to an intermediate is only a monochloride that can be removed; thus, an objective substance can be purified easily.

The chlorine content of 2mDBTBPDBq-II, which is an objective substance in this embodiment, was measured by combustion-ion chromatography. According to the measurement, the chlorine content of 2mDBTBPDBq-II was 1 ppm (1 μg/g), which was very small.

Example 2

Figure 8:
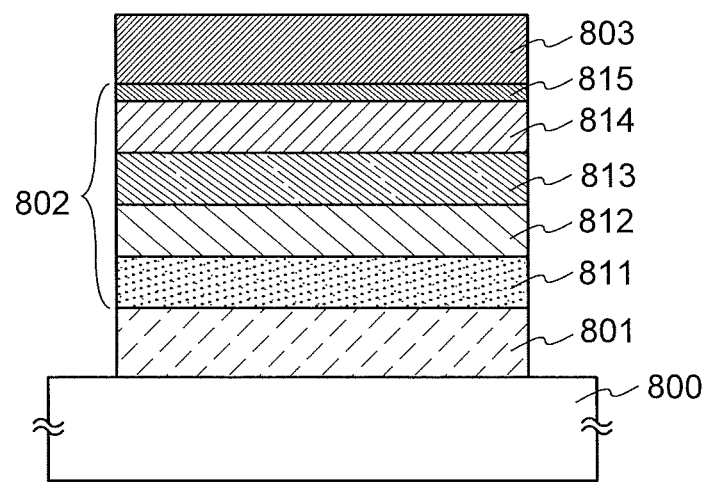
FIG. 8 illustrates a structure of each of a light-emitting element 1, a comparative light-emitting element 2, and a comparative light-emitting element 3.

In this example, a light-emitting element 1 of one embodiment of the present invention, and a comparative light-emitting element 2 and a comparative light-emitting element 3, which were fabricated for comparison, are described with reference to FIG. 8. Chemical formulae of materials used in this example are shown below.

[Chemical Formulae 19]

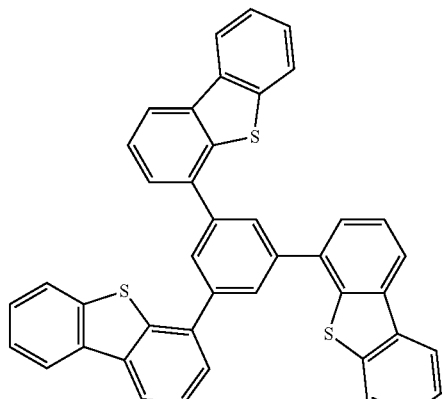

DBT3P-II

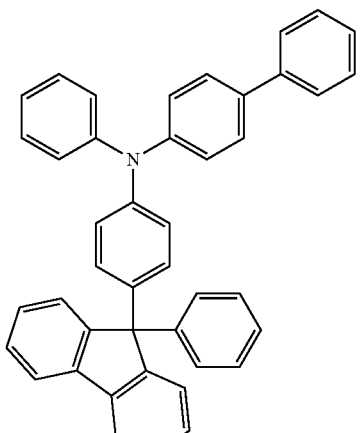

BPAFLP

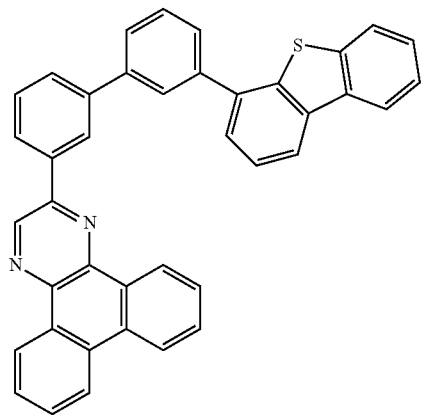

(200)

2mDBTBPDBq-II

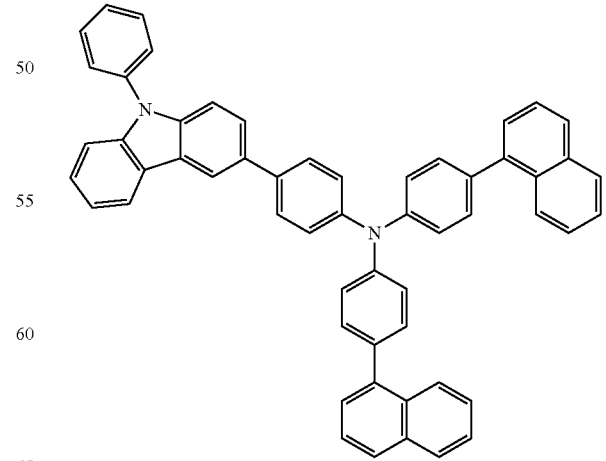

PCBNBB

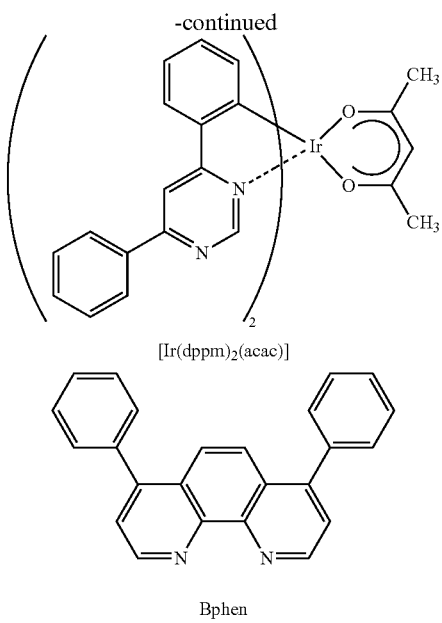

[Ir(dppm)₂(acac)]

Bphen

<<Fabrication of Light-Emitting Element 1, Comparative Light-Emitting Element 2, and Comparative Light-Emitting Element 3>>

First, indium tin oxide containing silicon oxide (ITSO) was deposited over a glass substrate 800 by a sputtering method, whereby a first electrode 801 functioning as an anode was formed. The thickness was 110 nm and the electrode area was 2 mm×2 mm.

Next, as pretreatment for fabricating the light-emitting element 1, the comparative light-emitting element 2, and the comparative light-emitting element 3 over the substrate 800, UV ozone treatment was performed for 370 seconds after washing of a surface of the substrate with water and baking that was performed at 200° C. for 1 hour After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 800 was cooled down for approximately 30 minutes.

Next, the substrate 800 was fixed to a holder provided in the vacuum evaporation apparatus so that a surface of the substrate 1100 over which the first electrode 801 was formed faced downward. In this example, a case is described in which a hole-injection layer 811, a hole-transport layer 812, a light-emitting layer 813, an electron-transport layer 814, and an electron-injection layer 815, which are included in an EL layer 802, are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of DBT3P-II to molybdenum oxide was 4:2, whereby the hole-injection layer 811 was formed over the first electrode 801. The thickness was 20 nm. Note that co-evaporation is an evaporation method in which a plurality of different substances are concurrently vaporized from different evaporation sources.

Next, 4-phenyl-4'-(9-phenylfluoren-9-yl)triphenylamine (abbreviation: BPAFLP) was deposited by evaporation to a thickness of 20 nm, whereby the hole-transport layer 812 was formed.

Next, the light-emitting layer 813 was formed on the hole-transport layer 812. The light-emitting layer 813 that had a stacked-layer structure and a thickness of 40 nm was formed as follows: 2-[3'-(dibenzothiophen-4-yl)biphenyl-3-yl]dibenzo[f,h]quinoxaline (abbreviation: 2mDBTBPDBq-II), 4,4'-di(1-naphthyl)-4''-(9-phenyl-9H-carbazol-3-yl)triphenylamine (abbreviation: PCBNBB), and (acetylacetonato)bis(4,6-diphenylpyrimidinato)iridium(III) (abbreviation: [Ir(dppm)₂(acac)]) were deposited by co-evaporation so that the mass ratio of 2mDBTBPDBq-II to PCBNBB and [Ir(dppm)₂(acac)] was 0.7:0.3:0.05 to a thickness of 20 nm, and then 2mDBTBPDBq-II, PCBNBB, and [Ir(dppm)₂(acac)] were deposited by co-evaporation so that the mass ratio of 2mDBTBPDBq-II to PCBNBB and [Ir(dppm)₂(acac)] was 0.8:0.2:0.05 to a thickness of 20 nm.

Next, on the light-emitting layer 813, 2mDBTBPDBq-II was deposited by evaporation to a thickness of 20 nm and then bathophenanthroline (abbreviation: Bphen) was deposited by evaporation to a thickness of 10 nm, whereby the electron-transport layer 814 was formed. Furthermore, lithium fluoride was deposited by evaporation to a thickness of 1 nm on the electron-transport layer 814, whereby the electron-injection layer 815 was formed.

Note that 2mDBTBPDBq-II used for the light-emitting element 1 (the light-emitting layer 813 and the electron-transport layer 814) was synthesized by the synthesis method of one embodiment of the present invention, specifically, the synthesis method described in Example 1; on the other hand, 2mDBTBPDBq-II that was used for the comparative light-emitting element 2 and the comparative light-emitting element 3 was synthesized by a conventional synthesis method, specifically, a comparative synthesis method described in this example.

Finally, aluminum was deposited to a thickness of 200 nm on the electron-injection layer 815, whereby a second electrode 803 functioning as a cathode was formed. Through the above-described steps, the light-emitting element 1, the comparative light-emitting element 2, and the comparative light-emitting element 3 were fabricated. Note that in all the above evaporation steps, evaporation was performed by a resistance-heating method.

Table 1 shows element structures of the light-emitting element 1, the comparative light-emitting element 2, and the comparative light-emitting element 3 that were fabricated as described above.

TABLE 1

| | First electrode | Hole-injection layer | Hole-transport layer | Light-emitting layer | | Electron-transport layer | | Electron-injection layer | Second electrode |
|---|---|---|---|---|---|---|---|---|---|
| Light-emitting element 1 | ITSO (110 nm) | DBT3P-II:MoOx (4:2 20 nm) | BPAFLP (20 nm) | * | ** | 2mDBTBPDBq-II (Synthesis method of the present invention) (20 nm) | Bphen (10 nm) | LiF (1 nm) | Al (200 nm) |

TABLE 1-continued

| | First electrode | Hole-injection layer | Hole-transport layer | Light-emitting layer | | Electron-transport layer | Electron-injection layer | Second electrode |
|---|---|---|---|---|---|---|---|---|
| Comparative light-emitting element 2 | ITSO (110 nm) | DBT3P-II:MoOx (4:2 20 nm) | BPAFLP (20 nm) | *** | **** | 2mDBTBPDBq-II (Conventional synthesis method) (20 nm) | Bphen (10 nm) LiF (1 nm) | Al (200 nm) |
| Comparative light-emitting element 3 | ITSO (110 nm) | DBT3P-II:MoOx (4:2 20 nm) | BPAFLP (20 nm) | *** | **** | 2mDBTBPDBq-II (Conventional synthesis method) (20 nm) | Bphen (10 nm) LiF (1 nm) | Al (200 nm) |

\* 2mDBTBPDBq-II (Synthesis method of the present invention):PCBNBB:[Ir(dppm)$_2$(acac)] (0.7:0.3:0.05 20 nm)
\*\* 2mDBTBPDBq-II (Synthesis method of the present invention):PCBNBB:[Ir(dppm)$_2$(acac)] (0.8:0.2:0.05 20 nm)
\*\*\* 2mDBTBPDBq-II (Conventional synthesis method):PCBNBB:[Ir(dppm)$_2$(acac)] (0.7:0.3:0.05 20 nm)
\*\*\*\* 2mDBTBPDBq-II (Conventional synthesis method):PCBNBB:[Ir(dppm)$_2$(acac)] (0.8:0.2:0.05 20 nm)

The fabricated light-emitting element 1, comparative light-emitting element 2, and comparative light-emitting element 3 were each sealed in a glove box containing a nitrogen atmosphere so as not to be exposed to the air (specifically, a sealant was applied onto outer edges of the elements, and at the time of sealing, UV treatment was performed first and then heat treatment was performed at 80° C. for 1 hour).

<<Operation Characteristics of Light-Emitting Element 1, Comparative Light-Emitting Element 2, and Comparative Light-Emitting Element 3>>

Operation characteristics of the fabricated light-emitting element 1, comparative light-emitting element 2, and comparative light-emitting element 3 were measured. Note that the measurement was carried out at room temperature (in an atmosphere kept at 25° C.).

Figure 9:
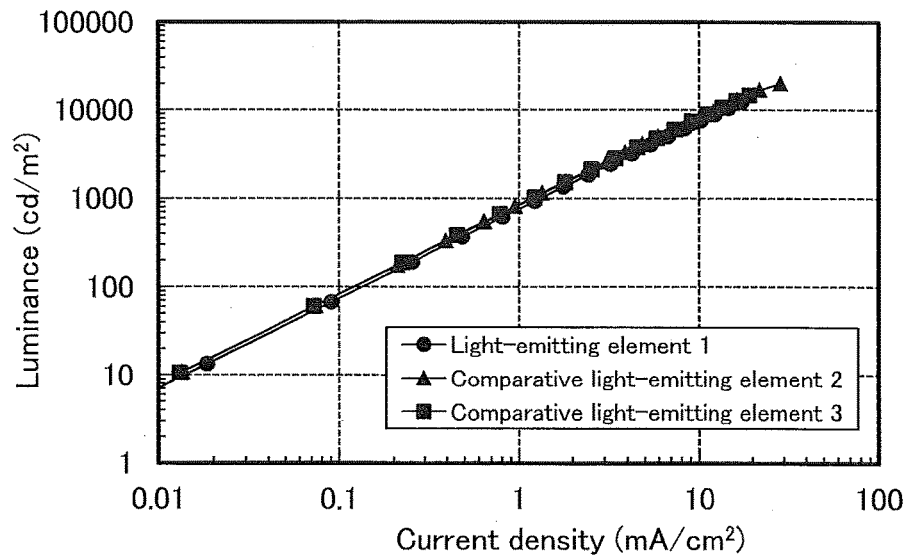
FIG. 9 shows current density-luminance characteristics of the light-emitting element 1, the comparative light-emitting element 2, and the comparative light-emitting element 3.
Figure 10:
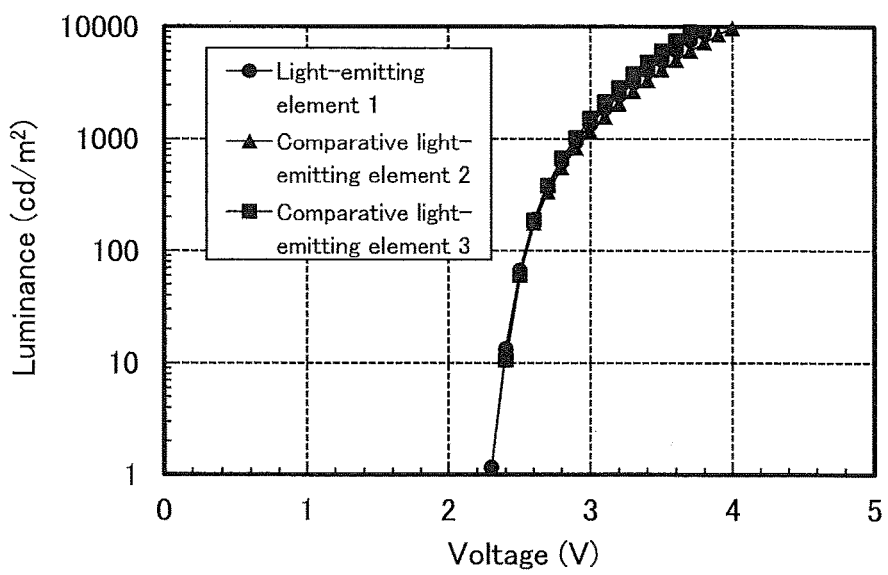
FIG. 10 shows voltage-luminance characteristics of the light-emitting element 1, the comparative light-emitting element 2, and the comparative light-emitting element 3.

FIG. 9 shows current density-luminance characteristics of the light-emitting element 1, the comparative light-emitting element 2, and the comparative light-emitting element 3. In FIG. 9, the vertical axis represents luminance (cd/m$^2$) and the horizontal axis represents current density (mA/cm$^2$). FIG. 10 shows current voltage-luminance characteristics of the light-emitting element 1, the comparative light-emitting element 2, and the comparative light-emitting element 3. In FIG. 10, the vertical axis represents luminance (cd/m$^2$) and the horizontal axis represents voltage (V).

Table 2 shows initial values of main characteristics of the light-emitting element 1, the comparative light-emitting element 2, and the comparative light-emitting element 3 at a luminance of approximately 1000 cd/m$^2$. Note that orange light emission originating from [Ir(dppm)$_2$(acac)] was obtained from each of the light-emitting elements.

Figure 11:
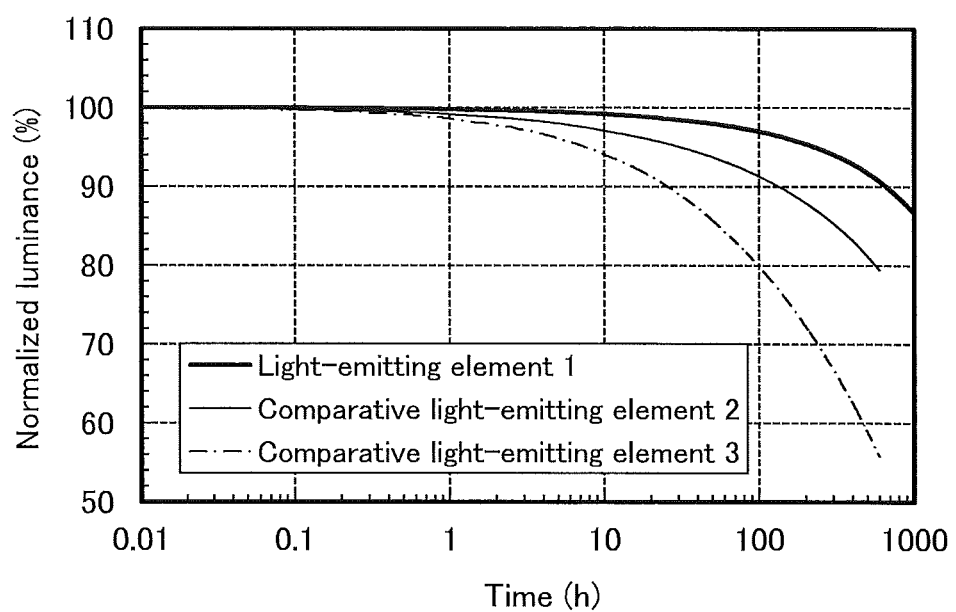
FIG. 11 shows reliability of each of the light-emitting element 1, the comparative light-emitting element 2, and the comparative light-emitting element 3.

FIG. 11 shows results of reliability tests of the light-emitting element 1, the comparative light-emitting element 2, and the comparative light-emitting element 3. In FIG. 11, the vertical axis represents normalized luminance (%) with an initial luminance of 100% and the horizontal axis represents driving time (h) of the elements. Note that in the reliability tests, the light-emitting element 1, the comparative light-emitting element 2, and the comparative light-emitting element 3 were driven under the conditions where the initial luminance was set to 5000 cd/m$^2$ and the current density was constant.

The light-emitting element 1 is a light-emitting element in which the EL layer contains, as an EL material, 2mDBTB-PDBq-H synthesized by the synthesis method of one embodiment of the present invention, that is, a synthesis method in which a 2-(chloroaryl)dibenzo[f,h]quinoxaline derivative that can be separated and removed by purification by sublimation is used as a synthetic intermediate in a synthetic pathway. In contrast, the comparative light-emitting element 2 and the comparative light-emitting element 3 are light-emitting elements in which the EL layer contains, as an EL material, 2mDBTBPDBq-II synthesized by the conventional synthesis method described as a reference example in this example. The results show that the light-emitting element 1 fabricated using, as the EL material, 2mDBTBPDBq-H synthesized by the synthesis method of one embodiment of the present invention has higher reliability and a longer lifetime than the comparative light-emitting element 2 and the comparative light-emitting element 3.

(Reference Synthesis Method: Conventional Synthesis Method)

As a reference synthesis method, the conventional method of synthesizing 2-[3'-(dibenzothiophen-4-yl)biphenyl-3-yl]dibenzo[f,h]quinoxaline (abbreviation: 2mDBTBPDBq-II) is described below.

TABLE 2

| | Voltage (V) | Current (mA) | Current density (mA/cm$^2$) | Luminance (cd/m$^2$) | Current efficiency (cd/A) | Power efficiency (lm/W) |
|---|---|---|---|---|---|---|
| Light-emitting element 1 | 2.8 | 0.032 | 0.81 | 620 | 76 | 86 |
| Comparative light-emitting element 2 | 3.0 | 0.054 | 1.4 | 1200 | 86 | 90 |
| Comparative light-emitting element 3 | 2.9 | 0.049 | 1.2 | 1000 | 84 | 91 |

[Chemical Formula 20]

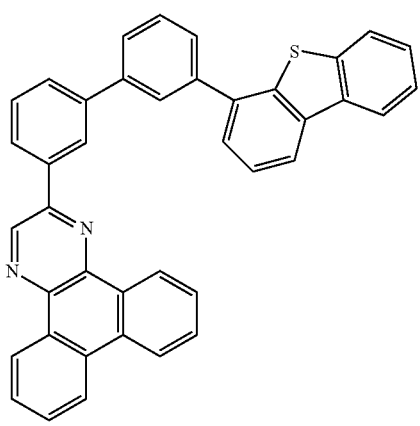

2mDBTBPDBq-II

<<Synthesis of 2mDBTBPDBq-II>>

Synthesis Scheme (b-1) of 2mDBTBPDBq-II is shown.

[Chemical Formulae 21]

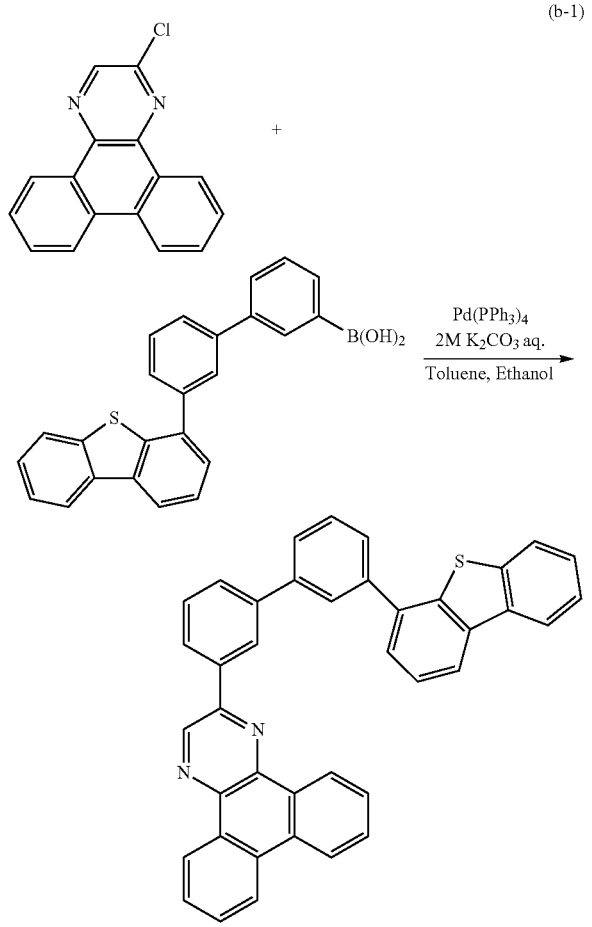

2mDBTBPDBq-II
(200)

In a 200-mL three-neck flask were put 0.83 g (3.2 mmol) of 2-chlorodibenzo[f,h]quinoxaline, 1.3 g (3.5 mmol) of 3'-(dibenzothiophen-4-yl)-3-biphenylboronic acid, 40 mL of toluene, 4 mL of ethanol, and 5 mL of a 2M aqueous potassium carbonate solution. This mixture was degassed by being stirred under reduced pressure, and the air in the flask was replaced with nitrogen. To this mixture was added 80 mg 70 μmol) of tetrakis(triphenylphosphine)palladium(0). This mixture was stirred at 80° C. under a nitrogen stream for 16 hours. After a predetermined period of time had elapsed, the precipitated solid was separated by filtration to give a yellow solid. Ethanol was added to this solid, followed by irradiation with ultrasonic waves. The solid was suction filtered to give a solid. The obtained solid was dissolved in toluene, and the toluene solution was suction filtered through alumina and Celite (produced by Wako Pure Chemical Industries, Ltd., Catalog No. 531-16855), and the filtrate was concentrated to give a yellow solid. Furthermore, this solid was recrystallized from toluene to give 1.1 g of yellow powder in a yield of 57%.

By a train sublimation method, 40.3 g of yellow powder, which was obtained by increasing the reaction scale in the above-described synthesis method, was purified. In the purification by sublimation, the yellow powder was heated at 350° C. under a pressure of 7.6 Pa with an argon flow rate of 100 mL/min. By the purification by sublimation, 6.4 g of the yellow powder, which was an objective substance, was obtained in a yield of 15.9% in a region heated at a temperature higher than 310° C. and lower than or equal to 345° C. in an apparatus (hereinafter, a high-temperature region) and 2.9 g of the yellow powder was obtained in a yield of 7.2% in a region heated at 310° C. in the apparatus (hereinafter, a middle-temperature region).

Here, the purity of 2-chlorodibenzo[f,h]quinoxaline, which was a source material, was analyzed by ACQUITY Ultra Performance LC (ACQUITY UPLC). According to the analysis, in addition to 2-chlorodibenzoquinoxaline, substances with m/z (i.e., mass-to-charge ratio) of 232 and 299 were contained as impurities with area ratios of 0.4% and 0.9%, respectively, and the purity was calculated to be 98.7%. These impurities with m/z of 232 and 299 are presumed to be dibenzo[f,h]quinoxaline and monochlorinated 2-chlorodibenzo[f,h]quinoxaline (Structural Formula (303)). Structural Formula (303) is shown below, respectively. The above results indicate that the 2-chlorodibenzo[f,h]quinoxaline derivative such as 2-chlorodibenzo[f,h]quinoxaline that was a source material generally contains a dihalide represented by Structural Formula (303) as an impurity.

[Chemical Formula 22]

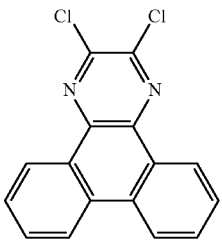

(303)

The purity of 2mDBTBPDBq-II obtained by the above synthesis and purification methods was analyzed by high performance liquid chromatography (UPLC). In the purity analysis, as an impurity, a substance with m/z (i.e., mass-to-charge ratio) of 599 was detected from a sample collected in the high-temperature region in the purification by sublimation with an area ratio lower than 0.1% and detected from a sample collected in the middle-temperature region with an area ratio of 0.1%.

In addition, when chlorine was quantified by a combustion-ion chromatography method in order to measure the halogen concentration of 2mDBTBPDBq-II, 63 ppm of chlorine was detected in the sample collected in the high-temperature region in the purification by sublimation and 276 ppm of chlorine was detected in the sample collected in the middle-temperature region in the purification by sublimation.

From the above results, the impurity is presumed to be monochlorinated 2mDBTBPDBq-II (Structural Formula (304)). Structural Formula (304) is shown below. The above results show that monochlorinated 2-chlorodibenzo[f,h]quinoxaline (Structural Formula (303)), which is contained in the source material, reacts with one equivalent of a boronic acid, so that the EL material (2mDBTPDBq-II that is the objective substance) containing chlorine as a substituent remains as an impurity. In addition, the above data on the comparative light-emitting element 2 and the comparative light-emitting element 3 indicate that a chloride of the EL material that contains chlorine as a substituent adversely affects the reliability of the elements. The above data also indicate that the luminance of the comparative light-emitting element 3 that used the sample collected in the middle-temperature region in the purification by sublimation and had a high chlorine content of the EL material of 276 ppm decays faster than the luminance of the comparative light-emitting element 2 that used the sample collected in the high-temperature region in the purification by sublimation and had a chlorine content of the EL material of 63 ppm.

Thus, it is indicated that the chlorine content of the EL material quantitatively correlates with the reliability (deterioration rate) of the element and that the synthesis method of one embodiment of the present invention that can decrease the chlorine content to be lower than or equal to 10 ppm can minimize the deterioration rate of the element and achieve high reliability of the element.

[Chemical Formula 23]

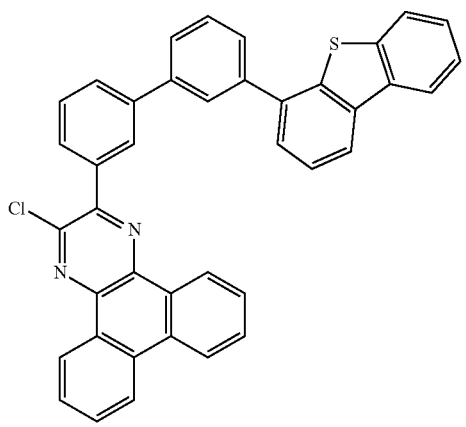

(304)

It was found from the above results that, as described in Embodiment 1, when reaction shown in Synthesis Scheme (B-1) is performed using a 2-chlorodibenzo[f,h]quinoxaline derivative (General Formula (A1)) containing a chlorinated (monochlorinated or dichlorinated) 2-chlorodibenzo[f,h]quinoxaline derivative (General Formula (A1')), a chlorinated dibenzo[f,h]quinoxaline derivative (General Formula (G1')) is generated as shown in Synthesis Scheme (B-1'). It was also found that the chlorinated dibenzo[f,h]quinoxaline derivative (General Formula (G1')) has a significant adverse effect on the reliability of a light-emitting element.

<<Chlorine Content of EL Material and Operation Characteristics of Light-Emitting Element>>

Furthermore, a correlation between the chlorine content of an EL material and the reliability of a light-emitting element was examined in detail.

Samples of 2mDBTBPDBq-II, which was used for the light-emitting element in this example, were synthesized in a plurality of lots, and the chlorine contents of the samples were measured by a combustion-ion chromatography method.

Four kinds of samples (samples 1 to 4) that are 2mDBT-BPDBq-II synthesized by the synthesis method of one embodiment of the present invention all had a very small chlorine content of 1 ppm (µg/g). In addition, six kinds of samples (samples 5 to 10) that are 2mDBTBPDBq-II synthesized by a conventional synthesis method described below had chlorine contents shown in Table 3.

TABLE 3

| Sample No. | Normalized luminance (%) | Chlorine content (ppm) | Light-emitting element |
|---|---|---|---|
| Sample 1 | 94.13 | 1 | Light-emitting element 1 |
| Sample 2 | 93.66 | 1 | Light-emitting element 2 |
| Sample 3 | 91.97 | 1 | Light-emitting element 3 |
| Sample 4 | 95.63 | 1 | Light-emitting element 4 |
| Sample 5 | 81.96 | 45 | Light-emitting element 5 |
| Sample 6 | 82.16 | 63 | Light-emitting element 6 |
| Sample 7 | 80.38 | 71 | Light-emitting element 7 |
| Sample 8 | 72.16 | 137 | Light-emitting element 8 |
| Sample 9 | 65.02 | 208 | Light-emitting element 9 |
| Sample 10 | 60.66 | 276 | Light-emitting element 10 |

Light-emitting elements (light-emitting elements 1 to 10) were fabricated using these samples (samples 1 to 10) and subjected to reliability tests for 450 hours. Note that structures of the fabricated light-emitting elements and conditions of the reliability tests are the same as those described above.

Figure 13:
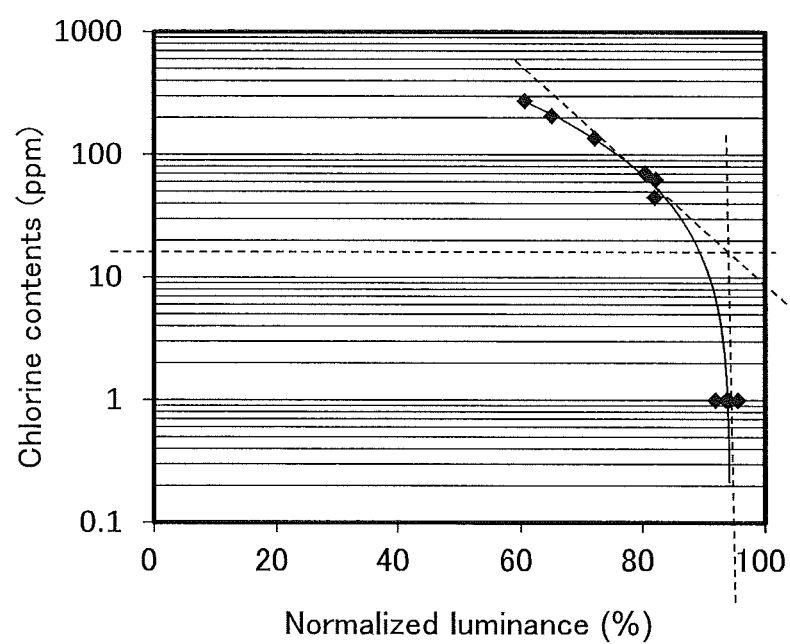
FIG. 13 shows correlations between the chlorine contents of EL materials and the reliability of light-emitting elements.

In FIG. 13, the normalized luminance (%) of the light-emitting elements after 450 hours and the chlorine contents (ppm) in the samples used for the light-emitting elements were plotted on the horizontal axis and the vertical axis, respectively, and an approximate curve obtained from the plot is shown. The approximate curve shows that the reliability increases as the chlorine content decreases in the region where the chlorine content is higher than approximately 10 ppm to 20 ppm, meanwhile the reliability is close to or reaches the saturation point when the chlorine content is lower than or equal to 10 ppm. This means that stable high reliability can be obtained by decreasing the chlorine content of an EL material to be less than or equal to 10 ppm.

Example 3

Synthesis Example 2

In this example, a method of synthesizing 2-[3'-(dibenzothiophen-4-yl)biphenyl-3-yl]dibenzo[f,h]quinoxaline (abbreviation: 2mDBTBPDBq-II) (Structural Formula (200)) is described as a synthesis method of one embodiment of the present invention. In the method described in this example, reaction conditions are different from those in Example 1. Note that a structure of 2mDBTBPDBq-II is shown below.

[Chemical Formula 24]

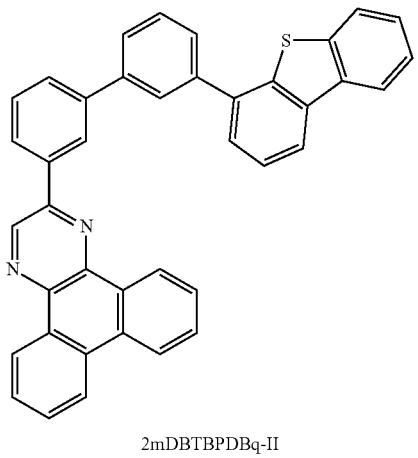

(200)

2mDBTBPDBq-II

Step 1: Synthesis of 2-(3-chlorophenyl)dibenzo[f,h]quinoxaline

First, 132.4 g (500 mmol) of 2-chlorodibenzo[f,h]quinoxaline (Structural Formula (301)), 86.0 g (550 mmol) of 3-chlorophenyl boronic acid, 159.0 g (1.5 mol) of potassium carbonate, 2.5 L of toluene, 630 mL of ethanol, and 750 mL of water were put in a 1-L three-neck flask. This mixture was degassed under reduced pressure, and then the air in the flask was replaced with nitrogen.

Then, 2.23 g (10 mmol) of palladium(II) acetate (abbreviation: Pd(OAc)$_2$) and 8.85 g (20 mmol) of tris(2,6-dimethoxyphenyl)phosphine were added to the mixture, and this mixture was heated and refluxed for approximately 4 hours. After that, the temperature of the flask was cooled down to room temperature, and a precipitate was separated by filtration. The precipitate was washed with water, ethanol, and toluene. The resulting residue was dissolved in heated toluene, and this solution was filtered through Celite. The obtained filtrate was cooled down to room temperature, and a precipitate was separated by filtration. The resulting residue was dried at 100° C. under reduced pressure to give 149.5 g of a pale yellow solid, which was an objective substance, in a yield of 88%.

Synthesis Scheme (c-1) of Step 1 is shown below.

[Chemical Formulae 25]

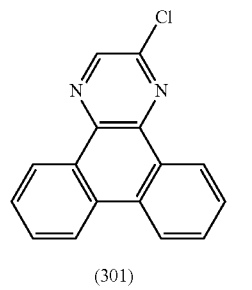

(301)

(c-1)

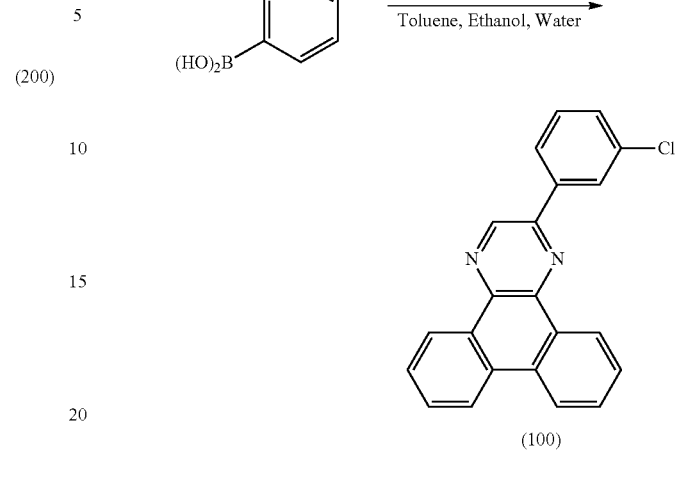

(100)

The pale yellow solid obtained in Step 1 was analyzed by nuclear magnetic resonance ($^1$H-NMR) spectroscopy to confirm that 2-(3-chlorophenyl)dibenzo[f,h]quinoxaline (Structural Formula (100)) was obtained in Step 1.

Step 2: Synthesis of 2-[3'-(dibenzothiophen-4-yl)biphenyl-3-yl]dibenzo[f,h]quinoxaline (abbreviation: 2mDBTBPDBq-II)

Next, 35.0 g (103 mmol) of 2-(3-chlorophenyl)dibenzo[f,h]quinoxaline obtained in Step 1, 33.5 g (110 mmol) of 3-(dibenzothiophen-4-yl)phenylboronic acid, 63.7 g (300 mmol) of tripotassium phosphate, 29 mL of t-butanol, and 670 mL of diethylene glycol dimethyl ether were put in a 1-L three-neck flask, and the air in the flask was replaced with nitrogen. This mixture was degassed by being stirred under reduced pressure.

Then, 0.69 g (3.1 mmol) of palladium(II) acetate and 2.22 g (6.2 mmol) of di(1-adamantyl)-n-butylphosphine (abbreviation: cataCXium®) were added to the mixture, and this mixture was heated and refluxed for approximately 8 hours. After that, the temperature of the flask was cooled down to room temperature, and a precipitate was separated by filtration. The precipitate was washed with water, ethanol, and toluene. The resulting residue was dissolved in heated toluene, and this solution was filtered through Celite. The obtained filtrate was cooled down to room temperature, and a precipitate was separated by filtration. The resulting residue was dried at 100° C. under reduced pressure to give 53.0 g of a pale yellow crystalline solid, which was an objective substance, in a yield of 94%.

By a train sublimation method, 110 g of the objective solid, which was obtained by increasing the reaction scale in the synthesis method, was purified. In the purification by sublimation, the objective substance was heated at 350° C. under a pressure of 5.6×10$^{-3}$ Pa. After cooling, 67.2 g of a pale yellow solid was obtained in a yield of 62%. Synthesis Scheme (c-2) of Step 2 is shown below.

[Chemical Formulae 26]

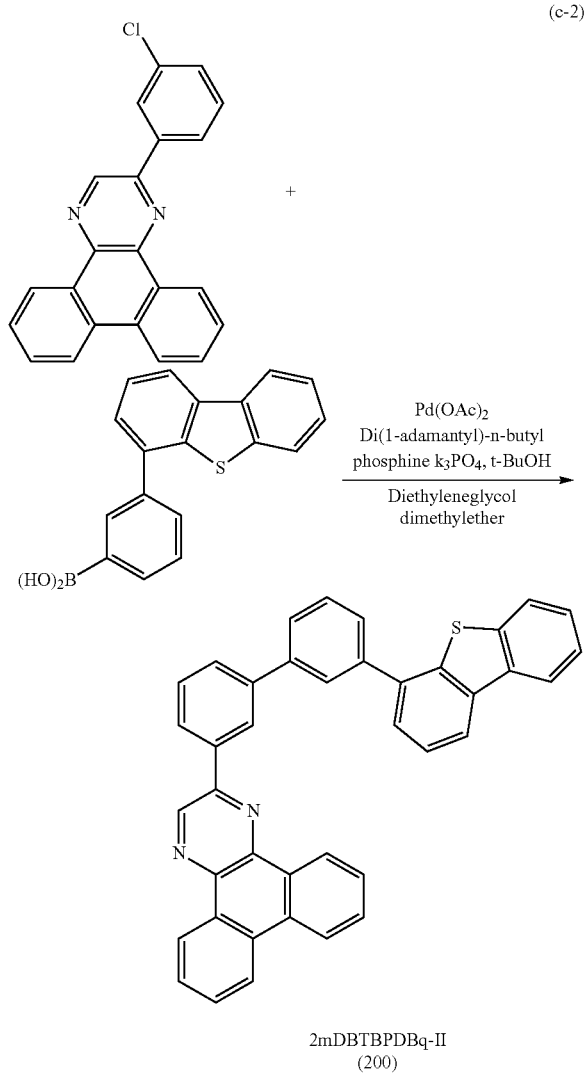

The pale yellow solid obtained in Step 2 was analyzed by nuclear magnetic resonance ($^1$H-NMR) spectroscopy to confirm that 2-[3'-(dibenzothiophen-4-yl)biphenyl-3-yl]dibenzo[f,h]quinoxaline (abbreviation: 2mDBTBPDBq-II) (Structural Formula (200)) was obtained.

Next, purity analysis of 2-(3-chlorophenyl)dibenzo[a]quinoxaline (Structural Formula (100)), which was the compound (i.e., intermediate) obtained in Step 1, was performed similarly. According to the analysis, in addition to 2-(3-chlorophenyl)dibenzo[f,h]quinoxaline (Structural Formula (100)), substances with m/z (i.e., mass-to-charge ratio) of 265, 307, 417, 459, and 611 were contained as impurities with area ratios of 0.2%, 0.2%, 0.1%, 0.1%, and 0.2%, respectively, and the purity was calculated to be 99.2%. The impurities with m/z of 265, 307, 417, 459, and 611 are presumed to be 2-chlorodibenzo[a]quinoxaline, 2-phenyldibenzo[f,h]quinoxaline, 2-(3-chlorophenyl)dibenzo[f,h]quinoxaline, 2-(1,1':3',1''-terphenyl)dibenzo[f,h]quinoxaline, and 2,2'-(1,1'-biphenyl-3,3'-diyl)di(dibenzo[f,h]quinoxaline). Note that these impurities are consumed in subsequent reaction or can be removed by purification. In addition, the results of the purity analysis indicate that an impurity (i.e., a chloride (a monochloride or a dichloride)) originating from the monochlorinated 2-chlorodibenzo[f,h]quinoxaline (Structural Formula (303)), which is an impurity that can be contained in the source material, i.e., 2-chlorodibenzo[f,h]quinoxaline (Structural Formula (301)), is hardly detected in the synthesis method.

The chlorine content of 2mDBTBPDBq-II, which is an objective substance in this embodiment, was measured by combustion-ion chromatography. According to the measurement, the chlorine content of 2mDBTBPDBq-II was 1 ppm (µg/g), which was very small. This indicates that the present invention can be implemented even when the reaction conditions are changed.

Example 4

Synthesis Example 3

A method of synthesizing 2-(4-chlorophenyl)dibenzo[f,h]quinoxaline represented by Structural Formula (101) in Embodiment 1 is described as a specific method of synthesizing a 2-(chloroaryl)dibenzo[f,h]quinoxaline derivative of one embodiment of the present invention that is a synthetic intermediate and can be separated and removed by purification by sublimation. Note that a structure of 2-(4-chlorophenyl)dibenzo[f,h]quinoxaline is shown below.

[Chemical Formula 27]

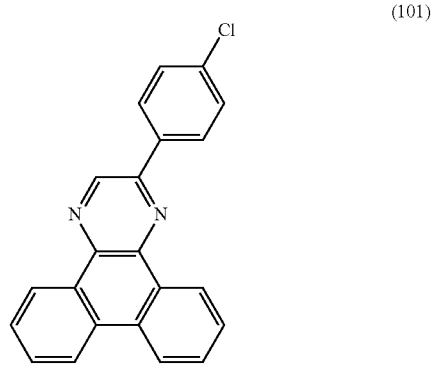

Step 2: Synthesis of
2-(4-chlorophenyl)dibenzo[f,h]quinoxaline

First, in a 200-mL three-neck flask were put 4.0 g (15 mmol) of 2-chlorodibenzo[f,h]quinoxaline (Structural Formula (301)), 2.5 g (17 mmol) of 4-chlorophenyl boronic acid, 76 mL of toluene, 19 mL of ethanol, and 22.7 mL of a 2M aqueous potassium carbonate solution. This mixture was degassed by being stirred under reduced pressure, and the air in the flask was replaced with nitrogen.

Then, 68 mg (15 mmol) of palladium(II) acetate (abbreviation: Pd(OAc)$_2$) and 0.18 g (0.60 mmol) of tris(2-methylphenyl)phosphine were added to the mixture. This mixture was stirred at approximately 80° C. under a nitrogen stream for 8 hours. After a predetermined period of time had elapsed, the precipitated solid was separated by filtration to give a brown solid. The obtained solid was dissolved in toluene, and the toluene solution was suction-filtered through alumina and Celite, and the filtrate was concentrated to give a yellow solid. Furthermore, this solid was recrystallized from toluene to give 3.8 g of the yellow solid in a yield of 75%.

Synthesis Scheme (d-1) of Step 2 is shown below.

[Chemical Formulae 28]

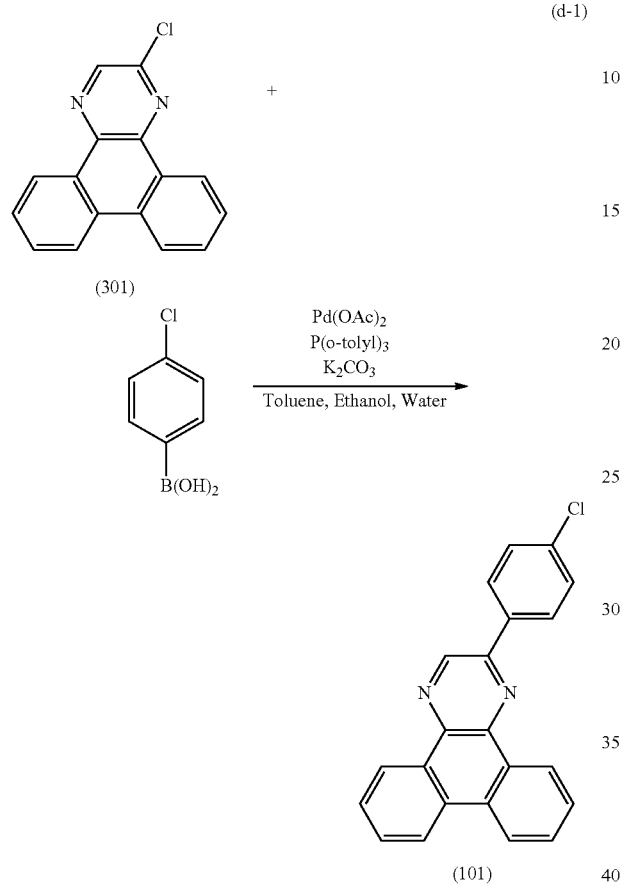

Figure 12A:
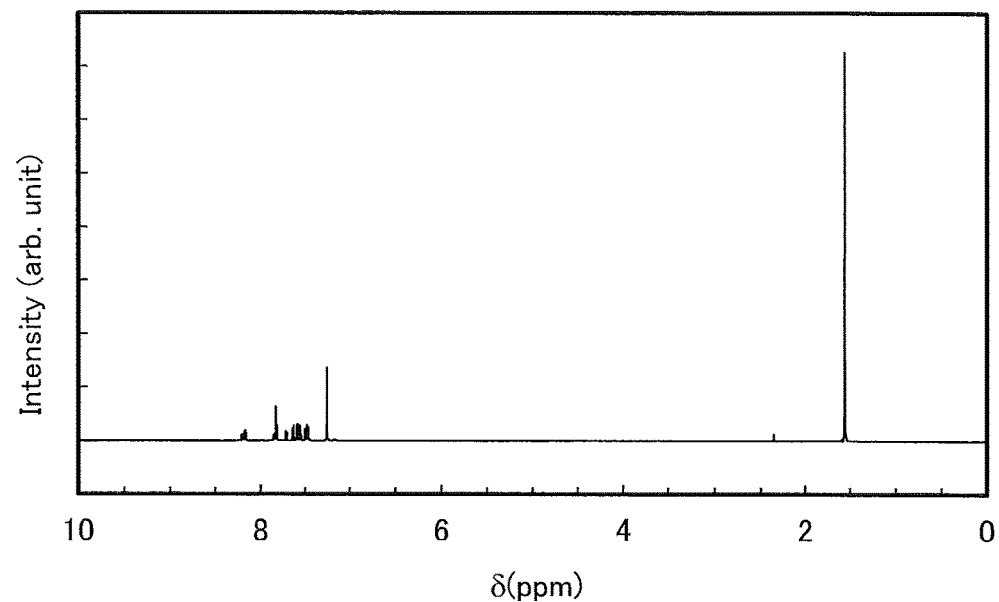
FIGS. 12A and 12B are $^1$H-NMR charts of an intermediate represented by Structural Formula (101).
Figure 12B:
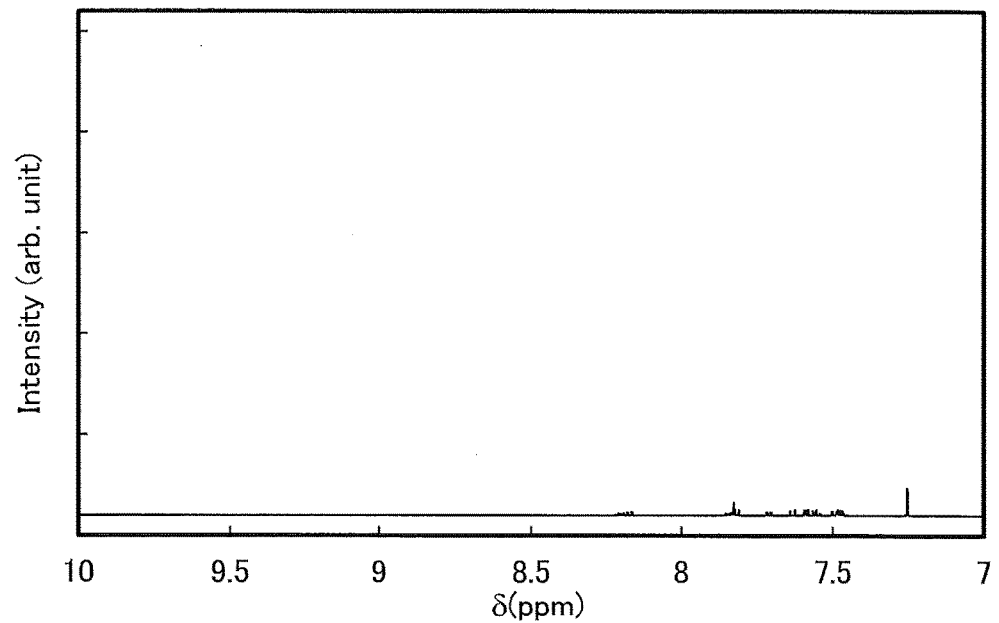

Analysis results by nuclear magnetic resonance ($^1$H-NMR) spectroscopy of the yellow solid obtained in Step 2 are described below. FIGS. 12A and 12B are $^1$H-NMR charts. FIG. 12B is a chart where the range from 6.5 (ppm) to 10 (ppm) on the horizontal axis (δ) in FIG. 12A is enlarged. The charts show that 2-(4-chlorophenyl)dibenzo[f,h]quinoxaline (Structural Formula (101)) was obtained in Step 2.

$^1$H NMR (CDCl$_3$, 500 MHz): δ (ppm)=7.45-7.50 (m, 3H), 7.54-7.60 (m, 3H), 7.64 (d, J=8.5 Hz, 1H), 7.71 (dd, J=8.0 Hz, 1.7 Hz, 1H), 7.82-7.86 (m, 3H), 8.17 (dd, J=8.0 Hz, 1.8 Hz, 1H), 8.19-8.23 (m, 1H).

This application is based on Japanese Patent Application serial No. 2013-190214 filed with the Japan Patent Office on Sep. 13, 2013 and Japanese Patent Application serial No. 2014-097738 filed with the Japan Patent Office on May 9, 2014, the entire contents of which are hereby incorporated by reference.

What is claimed is:

1. A method of synthesizing dibenzo[f,h]quinoxaline of formula (G1) containing 10 ppm or less of chlorine, comprising the steps of:

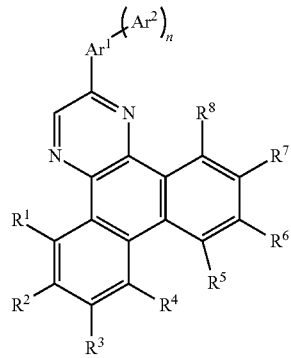

coupling a 2-chlorodibenzo[f,h]quinoxaline and a chloroaryl boronic acid of Formula (A2) to produce 2-(chloroaryl)dibenzo[f,h]quinoxaline of formula (G0), and

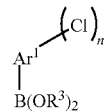

coupling the 2-(chloroaryl)dibenzo[f,h]quinoxaline of formula (G0) and an aryl boronic acid or a heteroaryl boronic acid of formula (A3)

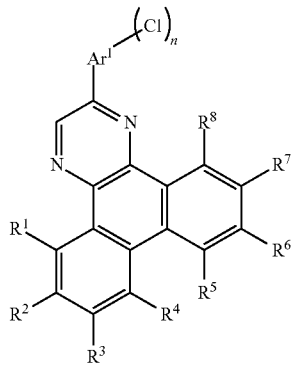

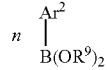

wherein Ar$^1$ represents a substituted or unsubstituted arylene group having 6 to 13 carbon atoms, Ar$^2$ represents a substituted or unsubstituted aryl group having 6 to 40 carbon atoms or a substituted or unsubstituted heteroaryl group having 6 to 40 carbon atoms, R$^1$ to R$^8$ independently represent hydrogen, an alkyl group having 1 to 6 carbon atoms, a phenyl group, or a phenyl group having an alkyl group having 1 to 6 carbon atoms as substituent, n is an integer of 1 to 3, each R$^9$ independently represents a hydrogen or an alkyl group or two R$^9$ in the same formula may be bonded together to form a ring with the oxygens to which they are attached.

* * * * *